US006916660B2

(12) United States Patent
Wang et al.

(10) Patent No.: US 6,916,660 B2
(45) Date of Patent: Jul. 12, 2005

(54) FLUORESCENT SENSOR COMPOUNDS FOR DETECTING SACCHARIDES

(75) Inventors: Binghe Wang, Apex, NC (US); Brent Weston, Durham, NC (US); Wenqian Yang, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 213 days.

(21) Appl. No.: 10/437,362

(22) Filed: May 13, 2003

(65) Prior Publication Data

US 2004/0048390 A1 Mar. 11, 2004

Related U.S. Application Data
(60) Provisional application No. 60/380,519, filed on May 14, 2002.

(51) Int. Cl.$^7$ .............................................. G01N 21/64
(52) U.S. Cl. ............................ 436/63; 436/64; 436/94; 436/95; 436/172
(58) Field of Search ............................... 436/63, 64, 94, 436/95, 172; 250/458.1, 459.1; 600/316, 317, 319

(56) References Cited

U.S. PATENT DOCUMENTS

| | | | | |
|---|---|---|---|---|
| 5,503,770 A | | 4/1996 | James et al. ............ | 252/301.16 |
| 5,512,246 A | * | 4/1996 | Russell et al. ................ | 422/57 |
| 5,939,290 A | | 8/1999 | Venot et al. .................... | 435/74 |
| 6,030,815 A | | 2/2000 | DeFrees et al. ............... | 435/97 |
| 6,183,994 B1 | | 2/2001 | Nilsson ........................ | 435/75 |
| 6,319,540 B1 | | 11/2001 | Van Antwerp et al. .... | 427/2.13 |
| 6,366,793 B1 | | 4/2002 | Bell et al. .................... | 600/317 |
| 6,387,672 B1 | | 5/2002 | Arimori et al. .............. | 435/183 |
| 6,534,316 B2 | * | 3/2003 | Strongin et al. .............. | 436/94 |
| 6,627,316 B1 | * | 9/2003 | Matsuki et al. .............. | 428/413 |
| 6,766,183 B2 | * | 7/2004 | Walsh et al. ................. | 600/317 |
| 2002/0043651 A1 | * | 4/2002 | Darrow et al. ............ | 252/408.1 |
| 2002/0094586 A1 | * | 7/2002 | Daniloff et al. ............. | 436/518 |
| 2002/0164671 A1 | | 11/2002 | James et al. .................. | 435/14 |

FOREIGN PATENT DOCUMENTS

| | | |
|---|---|---|
| WO | WO01/18543 | 3/2001 |
| WO | WO01/20334 | 3/2001 |
| WO | WO02/72588 | 9/2002 |

OTHER PUBLICATIONS

Prokai–Tatrai et al., "Design, Synthesis and Biological Evaluation of Novel, Centrally–Acting Thyrotropin–Releasing Hormone Analogues," *Bioorganic & Medicinal Chemistry Letters*, vol. 12, pp. 2171–2174 (Aug. 19, 2002).

Eggert et al., "A New Glucose–Selective Fluorescent Bisboronic Acid. First Report of Strong α–Furanose Complexation in Aqueous Solution at Physiological pH," *J. Org. Chem.*, vol. 64, pp. 3846–3852 (1999).

IPER for corresponding PCT Appl. No. PCT/US03/15093 dateed Jun. 17, 2004.

* cited by examiner

Primary Examiner—Jeffrey R. Snay
(74) Attorney, Agent, or Firm—Jenkins, Wilson & Taylor, P.A.

(57) ABSTRACT

Fluorescent sensor compounds having the formula:

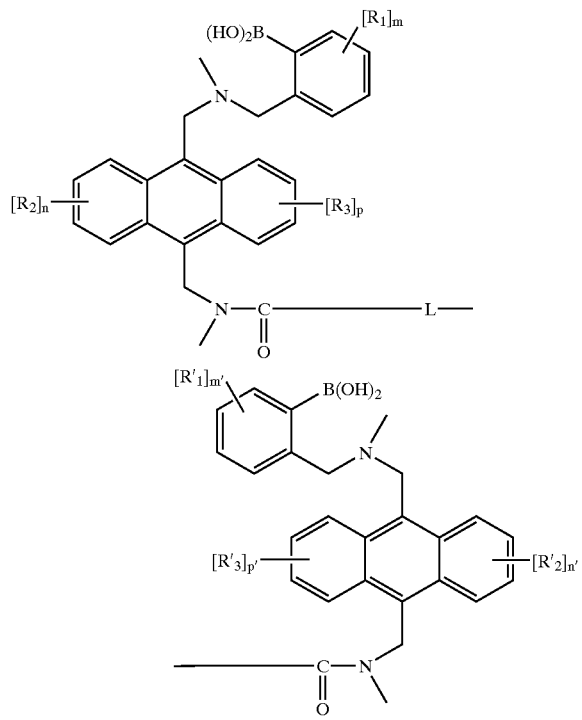

wherein L is selected from the group consisting of alkyl, alkylene, aryl, cycloalkyl, alkoxy, aryloxy, arylalkyl, and arylalkyloxyl;

each m, m', n, n', p, and p' is independently an integer from 0 to 4, inclusive; and each $R_1$, $R'_1$, $R_2$, $R'_2$, $R_3$ and $R'_3$ is independently selected from the group consisting of hydrogen, alkyl, alkylene, aryl, cycloalkyl, alkoxy, aryloxy, arylalkyl, arylalkyloxyl, halo, substituted and unsubstituted amino, and substituted and unsubstituted thiol, are useful for the selective detection of saccharides such as glucose and sialyl Lewis X. The compounds find particular use in detecting saccharides in biological samples, and in detecting cancer cells that express cell surface polysaccharides such as sialyl Lewis X.

25 Claims, 8 Drawing Sheets sialyl Lewis a (sLea) tetrasaccharide

Lewis Y (Ley) tetrasaccharide sialyl Lewis X (sLex) tetrasaccharide

Lewis X (Lex) trisaccharide

Scheme 1

(a) i. MeOH, THF, MeNH$_2$ (40%, wt), ii. NaBH$_4$, 90%; (b) MeOH, TEA, (Boc)$_2$O, 78%; (c) DMSO, TEA, Py·SO$_3$, 100%; (d) i. MeOH, THF, MeNH$_2$ (40%, wt), ii. NaBH$_4$, 83%. (e) CH$_2$Cl$_2$, EDC, HOOCRCOOH, 30–90%; (f) i. TFA, CH$_2$Cl$_2$, ii. CH$_3$CN, 8, K$_2$CO$_3$, 30–80%.

FLUORESCENT SENSOR COMPOUNDS FOR DETECTING SACCHARIDES

CROSS REFERENCE TO RELATED APPLICATIONS

The present patent application claims benefit of and priority to U.S. Provisional Application Ser. No. 60/380,519 entitled "DIBORONIC ACIDS AS FLUORESCENT PROBES FOR CELLS EXPRESSION SIALYL LEWIS X" which was filed May 14, 2002 and is incorporated herein by reference in its entirety.

GRANT STATEMENT

This invention was made in part from government support under Grant Nos. NO1-CO-27184, CA88343 and DK55062 from the National Institutes of Health. The U.S. Government has certain rights in the invention.

FIELD OF THE INVENTION

The present invention relates, in general, to fluorescent compounds that are useful in detecting saccharides. More particularly, the present invention relates to fluorescent compounds that selectively bind saccharides such as glucose and cell surface saccharides such as sialyl Lewis X, sialyl Lewis A, Lewis Y, and Lewis X, and methods that utilize these compounds.

| Table Of Abbreviations | |
|---|---|
| $\lambda_{ex}$ | excitation wavelength |
| $\lambda_{em}$ | emission wavelength |
| COSY | correlation spectroscopy |
| FBS | fetal bovine serum |
| FITC | fluorescein isothiocyanate |
| HCC | hepatocellular carcinoma |
| HMQC | heteronuclear multiple-quantum correlation |
| HMBC | heteronuclear multiple-bond correlation |
| $I_{rel}$ | relative fluorescent intensity |
| Lea | Lewis A |
| Lex | Lewis X |
| Ley | Lewis Y |
| PBS | phosphate-buffered saline |
| PET | photo-induced electron transfer |
| ROESY | rotating Overhauser effect spectroscopy |
| sLex | sialyl Lewis x |
| sLea | sialyl Lewis A |
| TOCSY | total correlation spectroscopy |

BACKGROUND ART

Carbohydrate molecules known as saccharides or sugars are clinically and physiologically important analytes that are implicated in numerous medical conditions and disorders. Monosaccharides, such as glucose and fructose, are saccharide monomers that form the basic structural units of more complex sugars. Monosaccharides are also clinically significant in their own right, due in part to their role in disorders such as diabetes. Polysaccharides are naturally ubiquitous molecules that are involved in diverse biological systems ranging from plant structure to blood-type grouping. Because of the widespread importance of saccharides, methods for reliably detecting their presence in a broad array of biological, chemical and clinical samples remains an ever-pressing need.

Cell-surface polysaccharides are but one important group of saccharides. As part of glycosylated proteins and lipids, these polysaccharides often form characteristic signatures of different cell types. See, Fukuda, M. (1992) *Cell Surface Carbohydrates and Cell Development* (Boca Raton: CRC); Fukuda, M. (1994) *Cell Surface Carbohydrates: Cell-type Specific Expression. In Molecular Glycobiology*, M. Fukuda, & O. Hindsgaul. eds. (New York: Oxford University, pp 1–52).

Certain cell surface carbohydrates, such as sialyl Lewis X (sLex), sialyl Lewis A (sLea), Lewis X (Lex) and Lewis Y (Ley) (structures illustrated in FIG. 1), have been associated with the development and progression of many types of cancers. See, Fukuda, M. (1992) *Cell Surface Carbohydrates in Hematopoietic Cell Differentiation and Malignancy. In Cell Surface Carbohydrates and Cell Development*, M. Fukuda. ed. (Boca Raton: CRC). pp 127–160; Dennis, J. W. (1992) *Changes in Glycosylation Associated with Malignant Transformation and Tumor progression. In Cell Surface Carbohydrates and Cell Development*, M. Fukuda. ed. (Boca Raton: CRC). pp 161–194; Jorgensen, T., et al., (1995) *Cancer Res.* 55, 1817–1819; Idikio, H. A. (1997) *Glycoconjugate J.* 14, 875–877; and El-Serag, H. B. and Mason, A. C. (1999) *New Engl. J. Med.* 340, 745–750. The cell-surface expression of these carbohydrates, which are important components of ligands involved in selectin-mediated cell adhesion and inflammatory responses, are specifically associated with the development and progression of human carcinomas such as hepatocellular carcinoma (HCC). See, Shacter, E. and Weitzman, S. A. (2002) *Oncology* 16, 217–223; Yago, K., et al. (1993) *Cancer Res.* 53, 5559–5565.

For example, normally differentiated hepatocytes do not express sLex, but chronically diseased liver expresses high levels of sLex, which is associated with a high degree of carcinogenicity. Fujiwara, Y. et al. (2002) *Hepatogastroenterology* 49, 213–217. Over-expression of sLex in chronic inflammatory diseases of the liver has been reported in several contexts by multiple investigators. Minta, J. O. et al. (1998) *Biochim. Biophys. Acta*. 1442, 286–295; Okada, Y. et al. (1994) *Cancer* 73, 1811–1816; and Jezequel-Cuer, M. et al. (1992) *Liver* 12, 140–146. Loss and gain of sLex expression in variously differentiated HCC specimens has also been well described.

However, the specific role(s) for sLex in transformation and progression to HCC are not entirely understood. Sensor compounds that could sensitively trace this development in vivo would likely further the understanding of hepatocarcinogenesis, in addition to providing new diagnostic and therapeutic approaches. Moreover, diagnosis and staging of HCC is often limited due to inability to detect advanced disease. Treatment of HCC is also impaired by lack of sensitive detection and further by drug-resistance. Nakakura, E. K. and Choti, M. A. (2000) *Oncology* 14, 1085–1098. Sensor compounds that selectively bind sLex could both recognize occult metastasis and provide targeted delivery of treatment, and thus may improve chances for success in treatment of this disease.

Antibodies specific for cell-surface polysaccharides have been used for the development of in vitro diagnostic and detection tools, targeted drug delivery vectors, and tissue-specific imaging agents. However, success in the in vivo application of antibody-based diagnostic and therapeutic agents has been limited partly because of their poor stability, immunogenicity, poor permeability, and complexity in chemical conjugation with the diagnostic or imaging agents. The development of small, organic molecule-based compounds capable of specific recognition of cell-surface biomarkers would be advantageous, as they generally possess more desirable pharmaceutical, biopharmaceutical, and chemical properties. Such sensor compounds would be useful for diagnostic labeling, drug delivery, and selective imaging applications, and could also be considered antibody mimics for the high specificity recognition of cell biomarkers such as sLex and other cell surface carbohydrates. Unfortunately, the development of selective sensor compounds for polysaccharides such as sLex has been very limited. See, e.g., Sugasaki, A. et al. (2001) *J. Am. Chem. Soc.* 123, 10239–10244. Possible reasons for this limited development include the complexity of polysaccharides and their conformational flexibility, which makes sensor construction difficult.

Among the monosaccharides, of particular medical and clinical interest is the monosaccharide glucose. The production and the consumption of glucose are regulated such that the concentration of glucose is relatively constant in the body fluids of normal or healthy mammals. A disruption of this regulation of glucose can be associated with diseases such as diabetes and hypoglycemia. One of the major challenges in the treatment of these diseases is the necessity to frequently monitor tissue glucose concentrations. The most commonly used technology for blood glucose concentration determination is an enzyme-based method, which requires frequent collection of blood samples. This is commonly accomplished by drawing a small blood sample (as by a fingerstick) several times daily. A patient typically uses a lancet or needle to draw a droplet of blood and applies the droplet to a reagent strip that is read in a small meter. This approach to glucose monitoring presents several problems, including inconvenience and resulting non-compliance by patients, and the fact that this method is not a continuous monitoring method.

Less invasive methods for measuring glucose in vivo have been described. These methods are generally based on the use of implanted sensor particles capable of generating a detectable analyte signal in response to the analyte concentration in the body. Moreover, there is presently a great deal of interest in the development of continuous glucose monitoring systems, which would be able to provide patients with instantaneous feedback and should help to improve the management of proper glucose concentration in diabetic patients. See, e.g., Koschinsky, T. et al. (2001) *Diabetes-Met. Res. Rev.* 17, 113–123; Gerritsen, M. et al. (1999) *Netherland J. Med.*, 54, 167–179; Daniloff, G. Y. (1999) *Diabetes Tech. Therap.* 1, 261–266; Atanasov, P. et al. (1997) *Biosen. Bioelectron.* 12, 669–680 and Kerner, W. Exp. (2001) *Clin. Endocrin. Diab.* 109, S341–S346 Suppl. 342. Devices capable of continuous glucose monitoring can be coupled to an insulin delivery device to achieve feedback-controlled delivery of insulin.

To develop a continuous monitoring system, it would be advantageous to use an implantable device that is in constant contact with biological fluid to give a continuous reading of glucose concentration. It is unlikely that the currently used enzyme-based methods could be incorporated into implantable devices, due to instability issues associated with protein-based products. See Gerritsen et al., supra. Non-enzymatic sensor compounds offer the advantage of higher stability and comparatively easy manufacturing. To develop chemical sensor-based continuous monitoring devices, sensor compounds that show high selectivity and appropriate affinity to glucose must be developed.

In view of the foregoing, there remains a need for compounds and methods for selectively detecting a variety of monosaccharides and polysaccharides. The high degree of structural similarity between different saccharides can hinder their selective detection. Color assays for saccharides are known, including those based on certain synthetic molecules and others based on enzymes that are known to bind of cleave saccharides. Enzymatic assays offer generally greater specificity than non-enzymatic color assays, but are usually more expensive and require greater care of reagents. For example, enzymes must be protected from extreme conditions during manufacture, storage and use. Ideally, the detection of saccharides involves compounds that are highly specific, highly selective and employ stable, non-enzymatic reagents.

Critical to the development of high affinity and high specificity sensors for saccharides is the need for recognition moieties that have strong interactions with the functional groups (e.g., hydroxyl groups) of a saccharide. Useful sensor molecules will generally also have a reporter moiety (e.g., a fluorophore), as well as a three-dimensional scaffolding moiety or "switch" that is mediated by a substrate recognition event (e.g., binding of the recognition moiety to a saccharide) and which triggers a reporting event.

With regard to the selection of a recognition moiety for a saccharide sensor compound, boronic acid has been known to have high affinity for diol-containing compounds such as carbohydrates. See Lorand, J. P. and Edwards, J. O. (1959) *J. Org. Chem.* 24, 769; Sugihara, J. M. and Bowman, C. M. (1958) *J. Am. Chem. Soc.* 80, 2443; Springsteen, G. and Wang, B. (2002) *Tetrahedron* 58, 5291–5300. By taking advantage of this strong interaction, several molecular recognition systems for carbohydrates based on boronic acid moieties have been developed. See, e.g., Wang, W. et al. (2002) *Current Org. Chem.* 6, 1285–1317; Yang, W. et al. (2003) *Med. Res. Rev.* 23, 346–368; James, T. D. et al. (1995) *J. Am. Chem. Soc.* 117, 8982–8987; James, T. D. et al. (1995) *Nature (London)* 374, 345–347; Eggert, H. et al. (1999) *J. Org. Chem.* 64, 3846–3852; Adhikiri, D. P. and Heagy, M. D. (1999) *Tetrahedron Lett.* 40, 7893–7896; Wiskur, S. L. and Anslyn, E. V. (2001) *J. Am. Chem. Soc.* 123, 10109–10110; Tong, A.-J. et al. (2001) *Anal. Chem.* 73, 1530–1536; Yang, W. et al. (2001) *Angew. Chem. Int. Ed.* 40, 1714–1718; DiCesare, N. and Lakowicz, J. R. (2001) *Org. Lett.* 3, 3891–3893; and Ward, C. J. et al. (2002) *Org. Lett.* 4, 477–479.

As stated above, once the recognition moiety of a sensor compound has bound its saccharide target, the binding should trigger a reporting event. It is known that anthracene fluorescence can be quenched by nitrogen lone pair electrons on an amino group (see schematic in FIG. 2). However, this quenching can be removed or reduced if lone pair electrons are masked through B—N bond formation. See James, T. D. et al. (1995) *J. Am. Chem. Soc.* 117, 8982–8987; Wulff, G. (1982) *Pure Appl. Chem.* 54, 2093–2102. Since binding with a carbohydrate is known to increase the acidity of boronic acid, the boronic ester formation will also increase the B—N bond strength, which results in the masking of the nitrogen lone pair electrons. Consequently, the fluorescence intensity of the anthracene system increases (FIG. 2).

Stated another way, the fluorescent intensity of the sensor compound changes in response to photo-induced electron transfer (PET) between the amine group and the fluorophore, as modulated by binding of saccharide hydroxyls to a pair of boronic acids. In the absence of saccharide binding, the fluorescence generated by the fluorescent group is quenched by the unshared electron pair of the nitrogen atom. When saccharide is bound, the unshared electron pair is utilized in the bond formation and does not participate in fluorescence-quenching. Consequently, intrinsic fluorescence of the sensor compound is expressed.

Boronic acid compounds have been used for the synthesis of glucose sensors. Among the significant development in the field are the diboronic acid sensors by the Shinkai group (see, James et al. (1995) supra, and James, T. D. et al. *Angew. Chem. Int Ed. Engl.* 1996, 35, 1910–1922); the Norrild group (see Norrild, supra; Eggert, supra; and Bielecki, M. et al. (1999) *J. Chem. Soc., Perkin Trans.* 2, 449–455); and the Drueckhammer group (see Yang (2001), supra). See also U.S. Pat. No. 5,503,770 to James et al.; U.S. Pat. No. 6,387,672 to James et al., U.S. Pat. No. 6,387,672 to Arimori et al., and International Patent Application Publication No. WO 01/20334 to Satcher et al, the disclosures of which are incorporated by reference.

The Shinkai and Norrild sensors showed enhanced fluorescence after binding with sugar, with a modest selectivity for glucose over other carbohydrates. For example, one sensor developed by the Shinkai group exhibited a 12- and 25-fold selectivity for glucose over fructose and galactose, respectively. The Drueckhammer system exhibited much higher selectivity for glucose over fructose and galactose than that of the Shinkai system. However, the fluorescence intensity of the sensor was reduced upon binding with sugars, which may limit its potential application. Recently, the Heagy group reported a monoboronic acid compound that showed the greatest spectroscopic changes with glucose compared to other sugars such as fructose. H Cao et al. (2002) *Org. Lett.* 4, 1503–1505. However, the binding constant of this compound with glucose was reported to be lower than that of fructose.

SUMMARY OF THE INVENTION

The present inventors have undertaken extensive investigations of the interaction of boronic acid and diols, and have achieved a much greater understanding of the factors that influence this complexation process. G. Springsteen and B. Wang (2002) *Tetrahedron* 58, 5291–5300. In the course of these investigations, the inventors successfully developed a new method of making fluorescent sensors for sugars through template-directed polymerization of boronic acid monomers. W. Wang et al. (1999) *Org. Lett.* 1, 1209–1212; S. Gao et al. (2001) *Bioorg. Chem.* 29, 308–320. Utilizing these methods, the inventors constructed novel fluorescent sensors by using selected spacers to link, through amide bond formation, two fluorescent boronic acid compounds. A number of dicarboxylic acid linkers with different length, rigidity, and spatial orientations were tested in order to find compounds with optimal arrangements for the selective detection of certain saccharides.

In view of the foregoing, the present invention, in a first aspect, provides fluorescent sensor compounds having the formula:

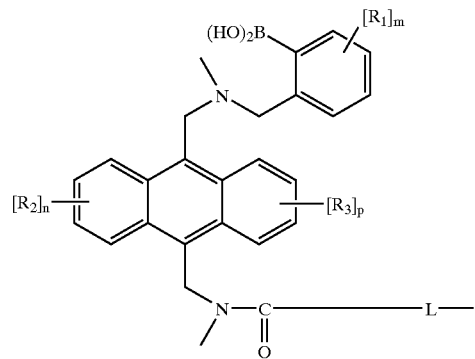

-continued

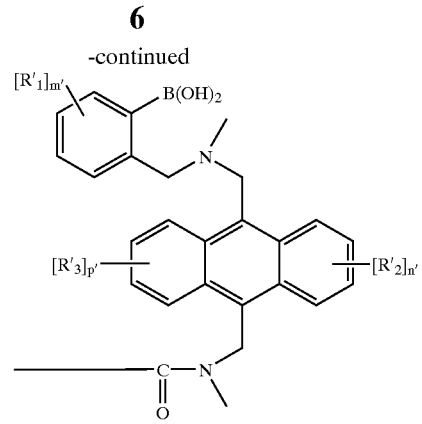

wherein L is selected from the group consisting of alkyl, alkylene, aryl, cycloalkyl, alkoxy, aryloxy, arylalkyl, and arylalkyloxyl groups;

each m, m', n, n', p, and p' is independently an integer from 0 to 4, inclusive; and each $R_1$, $R'_1$, $R_2$, $R'_2$, $R_3$ and $R'_3$ is independently selected from the group consisting of hydrogen, alkyl, alkylene, aryl, cycloalkyl, alkoxy, aryloxy, arylalkyl, arylalkyloxyl, halo, substituted and unsubstituted amino, and substituted and unsubstituted thiol groups.

In exemplary embodiments, the compounds of the invention selectively bind at least one saccharide. In particular, the inventive compounds are fluorescent sensor compounds that can undergo intramolecular electron transfer, which in turn modulates fluorescence as a function of the concentration of a saccharide analyte. Suitable saccharide analytes include but are not limited to monosaccharides such glucose and fructose, and polysaccharides such as sialyl Lewis X (sLex), sialyl Lewis A (sLea), Lewis X (Lex) and Lewis Y (Ley). The sensor compounds are designed so that photo-excited fluorophore and the boron atom moieties of the compound compete for unbonded amine electrons. In the absence of saccharide binding, electron transfer occurs predominantly with the fluorophore, causing fluorescent quenching and subsequently weak emission. When a saccharide is bound to the boronate groups, the average charge on the boron atoms becomes more positive, which increases the attraction of the unbonded electrons, preventing electron transfer. Fluorescent quenching is thus disabled, causing strong fluorescent emission.

In certain exemplary embodiments of the invention, the fluorescent compound having the structure set forth above selectively binds sialyl Lewis X; m, m', n, n', p, and p' are each zero, and the L group of the fluorescent compound is:

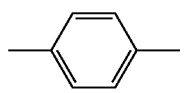

In other exemplary embodiments of the invention, the fluorescent sensor compound selectively binds glucose; m, m', n, n', p, and p' are each zero; and the L group of the fluorescent compound is

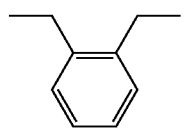

Methods of the present invention include methods for selectively binding glucose in a biological sample, methods for selectively binding sialyl Lewis X in a biological sample, and methods of detecting cancer cells that express sialyl Lewis X in a biological sample.

Thus, it is an object of the present invention to provide fluorescent sensor compounds that selectively bind saccharide compounds such as glucose and sialyl Lewis X.

An object of the invention having been stated hereinabove, and which is addressed in whole or in part by the present invention, other objects will become evident as the description proceeds when taken in connection with the accompanying drawings as best described hereinbelow.

DETAILED DESCRIPTION OF THE INVENTION

Figure 1:
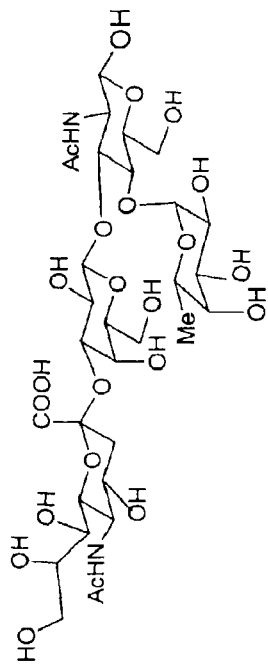
FIG. 1 illustrates the chemical structures of the Lewis oligosaccharides sialyl Lewis X (sLex), sialyl Lewis A (sLea), Lewis X (Lex) and Lewis Y (Ley).
Figure 1:
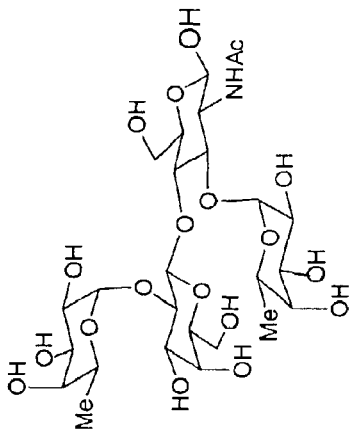
Figure 1:
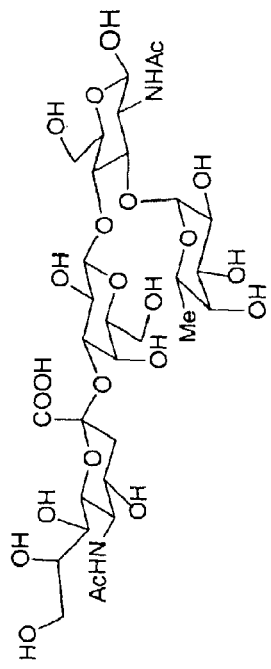
Figure 1:
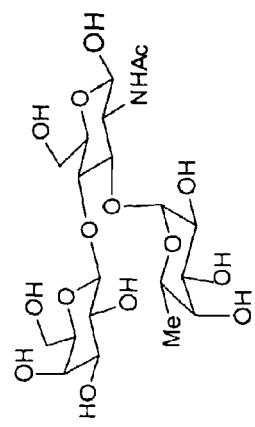
Figure 2:
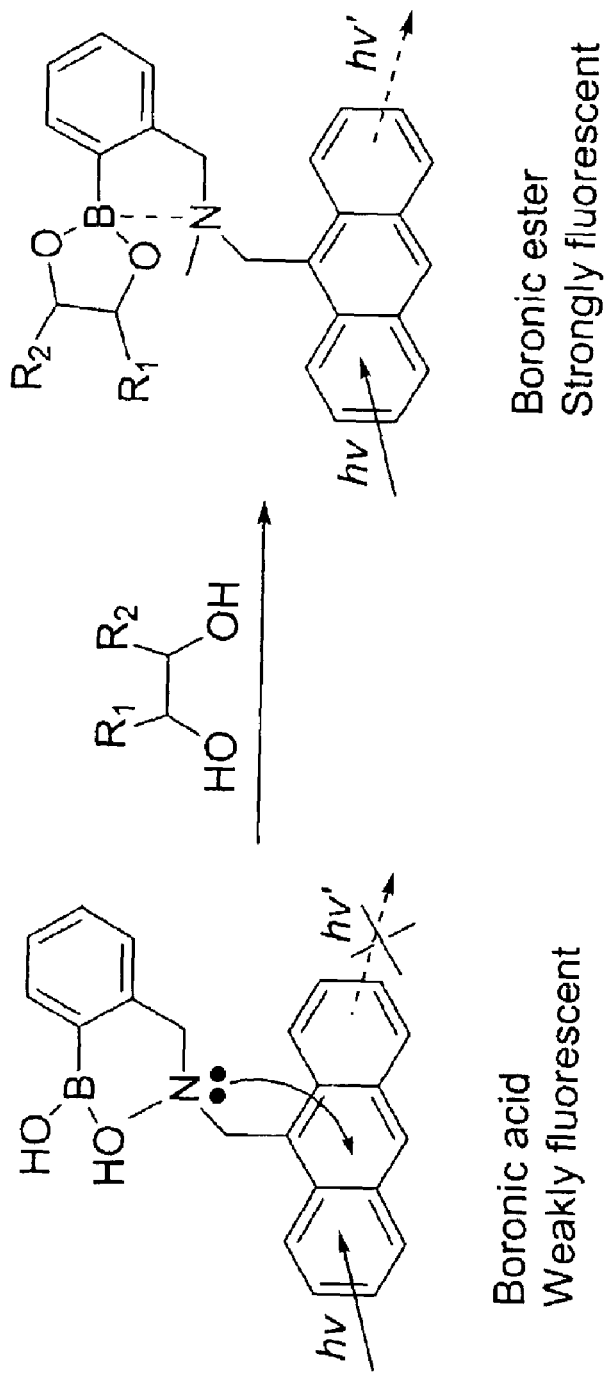
FIG. 2 is a schematic illustrating the photoinduced electron transfer (PET) and subsequent emission of fluorescence in response to the binding of a boronic acid moiety with a diol moiety.

The present invention will be now be described more fully hereinafter with reference to the accompanying Examples, in which preferred embodiments of the invention are shown. This invention can, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety.

Throughout the specification and claims, a given chemical formula or name shall encompass all optical and stereoisomers as well as racemic mixtures where such isomers and mixtures exist.

Disclosed herein is a compound of the Formula (I):

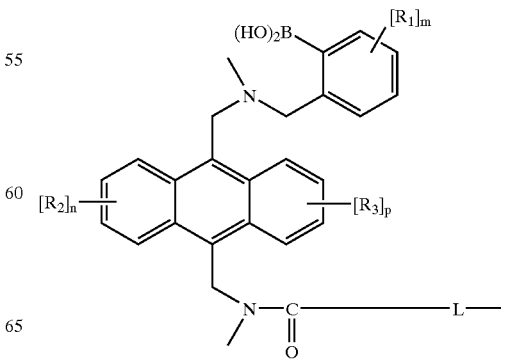

-continued

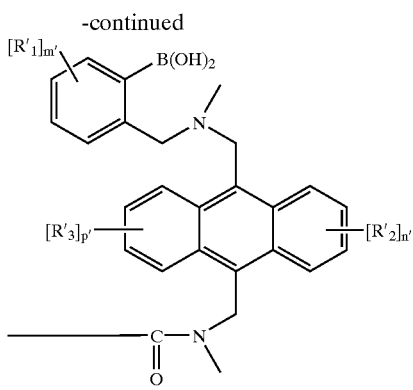

wherein L is selected from the group consisting of alkyl, alkylene, aryl, cycloalkyl, alkoxy, aryloxy, arylalkyl, and arylalkyloxyl groups;

each m, m', n, n', p, and p' is independently an integer from zero to four, inclusive; and each $R_1$, $R'_1$, $R_2$, $R'_2$, $R_3$ and $R'_3$ is independently selected from the group consisting of hydrogen, alkyl, alkylene, aryl, cycloalkyl, alkoxy, aryloxy, arylalkyl, arylalkyloxyl, halo, substituted and unsubstituted amino, and substituted and unsubstituted thiol groups.

By "independently selected," the skilled artisan will appreciate that each and every group may be selected from the entire list set forth as possible selections without regard to the selections of other groups having the same or different appellations. In other words, when there is more than one $R_1$ group (i.e., m>0), each $R_1$ group may be different from other $R_1$ groups, or may be the same as other $R_1$ groups. Similarly, as between an $R_1$ group and an $R_2$ group, for example, the $R_1$ group may be the same as the $R_2$ group or may be different from the $R_2$ group.

The skilled artisan will also appreciate that when m, m', n, n', p, or p' are zero, the resulting structure is the same as if m, m', n, n', p, or p', respectively, are four, but each "R" group on the respective ring is hydrogen. For example, when "m" is 0, this provides the same structure as if m were four but all possible $R_1$ groups are hydrogen.

As used herein the term "alkyl" refers to $C_{1-20}$ inclusive, linear, branched, or cyclic, saturated or unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. Exemplary alkyl groups have about 2 to about 20 carbon atoms.

The alkyl group can be optionally substituted with one or more alkyl group substituents which can be the same or different, where "alkyl group substituent" includes alkyl, halo, arylamino, acyl, hydroxy, aryloxy, alkoxyl, alkylthio, arylthio, aralkyloxy, aralkylthio, carboxy, alkoxycarbonyl, oxo and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl. "Branched" refers to an alkyl group in which a lower alkyl group, such as methyl, ethyl or propyl, is attached to a linear alkyl chain.

"Aryl" refers to an aromatic substituent that may be a single ring or multiple rings that are fused together, linked covalently, or linked to a common group such as an ethylene, methylene or oxy moiety. The aromatic rings of the aryl group may each and optionally contain heteroatoms. The aryl group can be optionally substituted with one or more aryl group substituents which can be the same or different, where "aryl group substituent" includes alkyl, aryl, arylalkyl, hydroxy, alkoxyl, aryloxy, arylalkoxyl, carboxy, acyl, halo, nitro, alkoxycarbonyl, aryloxycarbonyl, arylalkoxycarbonyl, acyloxyl, acylamino, aroylamino, carbamoyl, alkylcarbamoyl, dialkylcarbamoyl, arylthio, alkylthio, alkylene and ——NRR', where R and R' can be each independently hydrogen, alkyl, aryl and aralkyl. Aryl radicals may be attached to other moieties at any position on the aryl radical which would otherwise be occupied by a hydrogen atom. Specific examples of aryl groups include but are not limited to phenyl, naphthyl, anthracene, biphenyl, diphenylmethyl, 2,2-diphenyl-1-ethyl, quinoxalyl, cyclopentadienyl, furan, thiophene, pyrrole, pyran, pyridine, imidazole, isothiazole, isoxazole, pyrazole, pyrazine, pyrimidine, 2-pyridyl, 3-pyridyl, and the like.

As used herein, the terms "substituted alkyl" and "substituted aryl" include alkyl and aryl groups, as defined herein, in which one or more atoms or functional groups of the aryl or alkyl group are replaced with another atom or functional group, including for example, halogen, aryl, alkyl, alkoxyl, hydroxy, nitro, amino, alkylamino, dialkylamino, sulfate, and mercapto.

"Cyclic" and "cycloalkyl" refer to a non-aromatic mono- or multicyclic ring system of about 4 to about 10 carbon atoms. The cycloalkyl group can be optionally partially unsaturated. The cycloalkyl group can be also optionally substituted with an alkyl group substituent as defined herein, oxo and/or alkylene. There can be optionally inserted along the cyclic alkyl chain one or more oxygen, sulfur or substituted or unsubstituted nitrogen atoms, wherein the nitrogen substituent is hydrogen, lower alkyl, or aryl, thus providing a heterocyclic group. Representative monocyclic cycloalkyl rings include cyclopentyl, cyclohexyl and cycloheptyl. Preferred multicyclic cycloalkyl rings include adamantyl, octahydronaphthyl, decalin, camphor, camphane, and noradamantyl.

"Alkoxyl" refers to an alkyl-O—— group wherein alkyl is as previously described. The term "alkoxyl" as used herein can refer to $C_{1-20}$ inclusive, linear, branched, or cyclic, saturated or unsaturated oxo-hydrocarbon chains, including for example methoxy, ethoxy, propoxy, isopropoxy, butoxy, t-butoxy, and pentoxy.

"Aryloxyl" refers to an aryl-O—— group wherein the aryl group is as previously described. The term "aryloxyl" as used herein can refer to phenyloxyl or hexyloxyl, and alkyl, halo, or alkoxyl substituted phenyloxyl or hexyloxyl.

"Arylalkyl" refers to an aryl-alkyl-group wherein aryl and alkyl are as previously described. Exemplary arylalkyl groups include benzyl, phenylethyl and naphthylmethyl.

"Arylalkyloxyl" refers to an arylalkyl-O—— group wherein the arylalkyl group is as previously described. An exemplary aralkyloxy group is benzyloxy.

"Alkylene" refers to a straight or branched bivalent aliphatic hydrocarbon group having from 1 to about 20 carbon atoms. The alkylene group can be straight, branched or cyclic. The alkylene group can be also optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (——$CH_2$——); ethylene (——$CH_2$——

CH$_2$——); propylene (——(CH$_2$)$_3$——); cyclohexylene (——C$_6$H$_{10}$——); ——CH=CH——CH=CH——; ——CH=CH——CH$_2$——; ——(CH$_2$)$_n$——N(R)——(CH$_2$)$_m$——, wherein each of m and n is independently an integer from 0 to about 20 and R is hydrogen or lower alkyl; methylenedioxy (——O——CH$_2$——O——); and ethylenedioxy (——O——(CH$_2$)$_2$——O——). An alkylene group can have about 2 to about 3 carbon atoms and can further have 6–20 carbons.

The term "amino" as used herein, alone or in combination, means an optionally substituted ——NH$_2$ group. The amino group can be a primary, secondary or tertiary amino group containing substituents selected from hydrogen, alkyl, alkylene, aryl, acyl, arylalkyl, cycloalkyl, cycloarylalkyl radicals and the like. A primary amino has two free valences as hydrogen, i.e., ——NH$_2$. A secondary amino, which is also referred to as a mono-substituted amino or a N-substituted amino, has one free valence substituted as above. Tertiary amino, which is also referred to as a disubstituted amino or N,N-disubstituted amino, has two free valences substituted as above. For example, ——NH$_2$ is an unsubstituted amino, while ——N(H)(CH$_3$) is monosubstituted amino (N-methylamino) and ——N(CH$_3$)(CH$_2$-phenyl) is disubstituted amino (N-methyl-N-benzylamino). Substituted amino groups include, for example, methylamino, dimethylamino, ethylamino, diethylamino, dibutylamino, diallylamino, cyclohexylamino, acetylamino, propionylamino, benzoylamino, phenylamino and N-methyl-N-phenylamino.

As used herein, the term "thiol" means an ——SH group. Thiol groups may be substituted or unsubstituted, as set forth above. Substituted thiol groups include, for example, alkylthio groups, arylthio groups, heteroarylthio groups, arylalkylthio groups, heteroarylalkylthio groups and acylthio groups.

The terms "halo", "halide", or "halogen" as used herein refer to fluoro, chloro, bromo, and iodo groups.

As used herein, a "saccharide" may refer to a monosaccharide, a disaccharide, an oligosaccharide, or a polysaccharide. The term "oligosaccharide" refers to a polysaccharide having from 2 to about 10 saccharide units. Monosaccharides, or "simple sugars," include glucose, fructose, galactose, mannose, ribulose, threose, erythrose, arabinose, lyxose, allose, gulose and others known to those in the art. Particular saccharide units include, by way of example, all natural and synthetic derivatives or glucose, galactose, N-acetylglucosamine, N-acetylgalactosamine, fucose, sialic acid, 3-deoxy-D,L-octulosonic acid, and the like. Examples of other saccharides include saccharides containing at least one of an α- or β-glycosidically linked sialyl-, D-xylosyl-D-mannosyl-N-acetyl-D-glucosaminyl-, N-acetyl-D-galactosaminyl- or D-glucosyl group. Disaccharides include sucrose, maltose, and lactose. In the practice of the present invention, a preferred monosaccharide is glucose, while preferred polysaccharides include the cell-surface polysaccharides set forth in FIG. 1, namely, sialyl Lewis X (sLex), sialyl Lewis A (sLea), Lewis X and Lewis Y.

Saccharide units may be referred to herein by the following abbreviations: Ara=arabinosyl; Fru=fructosyl; Fuc=fucosyl; Gal=galactosyl; GalNAc=N-acetylgalacto; Glc=glucosyl; GlcNAc=N-acetylgluco; Man=mannosyl; Neu=Neuraminyl; and NeuAc=sialyl (N-acetylneuraminyl).

Figure 3:
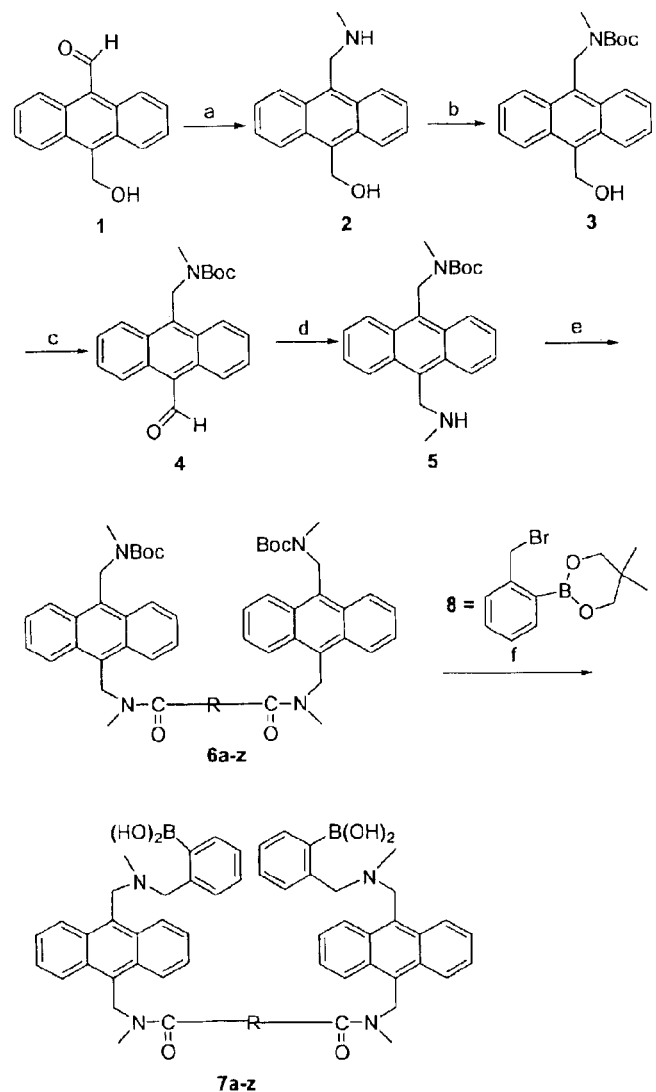
FIG. 3 depicts Scheme 1, which outlines a general synthesis of fluorescent sensor compounds of the present invention.

The synthesis of the inventive compounds is represented as Scheme 1 in FIG. 3, and is now generally described. Starting from the readily available hydroxyaldehyde 1 (Lin, Y.-I. et al. (1979) *J. Org. Chem.* 44, 4701–4703), upon reductive amination with methylamine in MeOH/THF and NaBH$_4$, amine 2 is obtained. The Boc-protected compound 3 is obtained by. treatment of 2 with di-tert-butyldicarbonate [(Boc)$_2$O] in MeOH in the presence of triethylamine (TEA). This is followed by oxidation with pyridine sulfur trioxide in dimethylsulfoxide (DMSO) in the presence of TEA to give aldehyde 4 in quantitative yield. The resulting aldehyde 4 is then converted to amine compound 5 in through reductive amination. Amine 5 is coupled with various diacids using 1-(2-dimethylaminopropyl)-3-ethylcarbodiimide hydrochloride (EDC) as the activating reagent to furnish compounds 6. After deprotection of compounds 6 with trifluoroacetic acid (TFA), the unprotected free amines are then reacted with boronate 8 (T. D. James et al. (1995) *J. Am. Chem. Soc.* 117, 8982–8987) in the presence of potassium carbonate to give the diboronic acids 7, shown in Table 1 below. This general synthesis is further described in the Examples section below.

TABLE 1

Chemical structures of diboronic acids 7a–z.

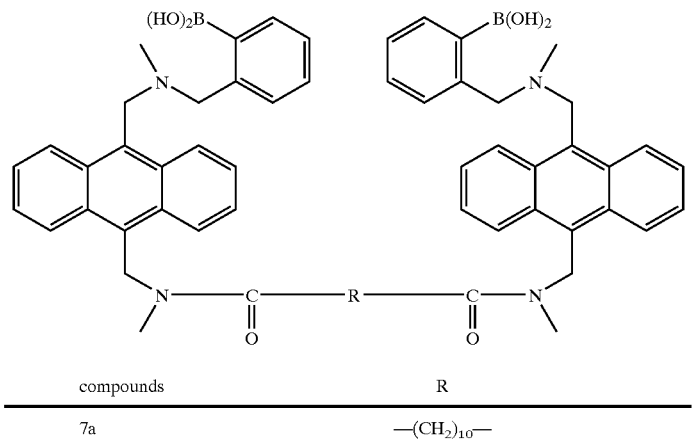

| compounds | R |
|---|---|
| 7a | —(CH$_2$)$_{10}$— |

TABLE 1-continued
Chemical structures of diboronic acids 7a–z.
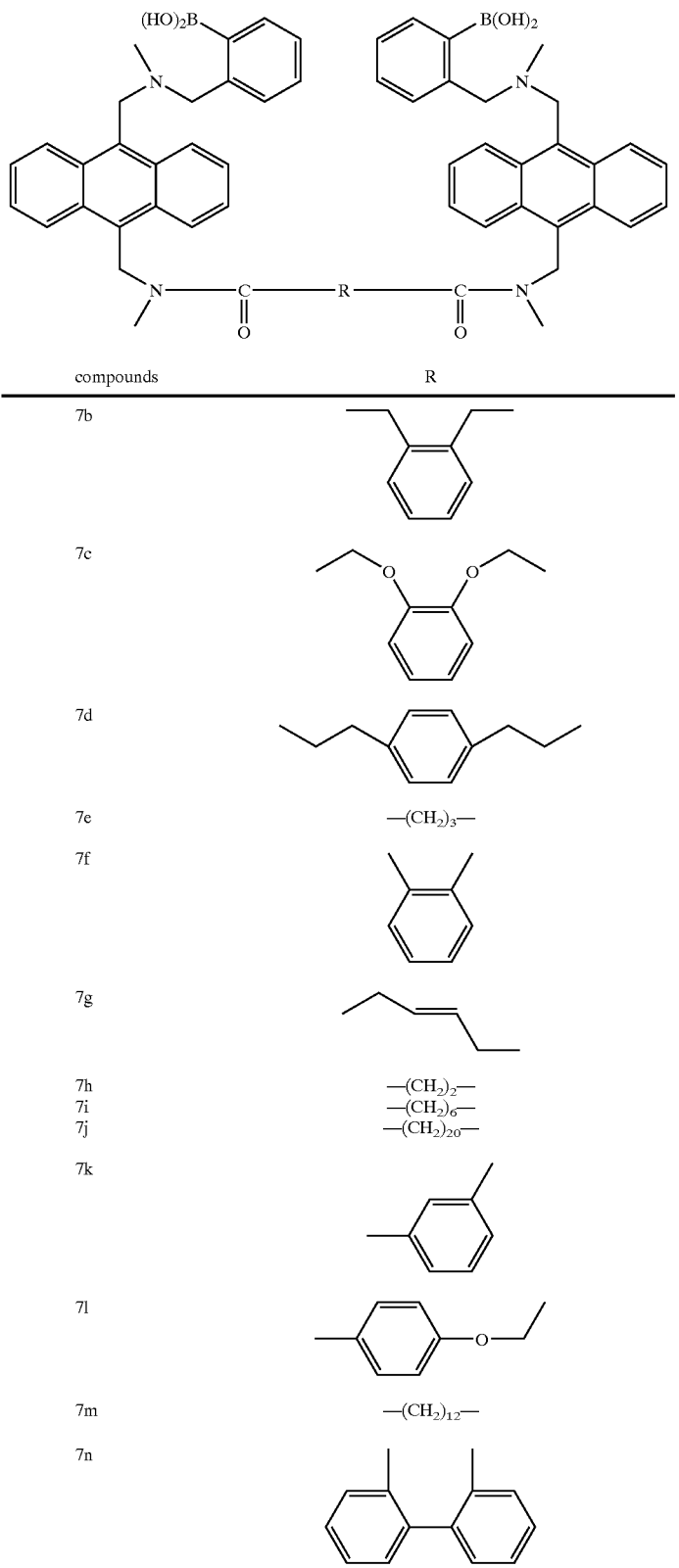
| compounds | R |
| --- | --- |
| 7b | |
| 7c | |
| 7d | |
| 7e | —(CH$_2$)$_3$— |
| 7f | |
| 7g | |
| 7h | —(CH$_2$)$_2$— |
| 7i | —(CH$_2$)$_6$— |
| 7j | —(CH$_2$)$_{20}$— |
| 7k | |
| 7l | |
| 7m | —(CH$_2$)$_{12}$— |
| 7n | |

TABLE 1-continued
Chemical structures of diboronic acids 7a–z.
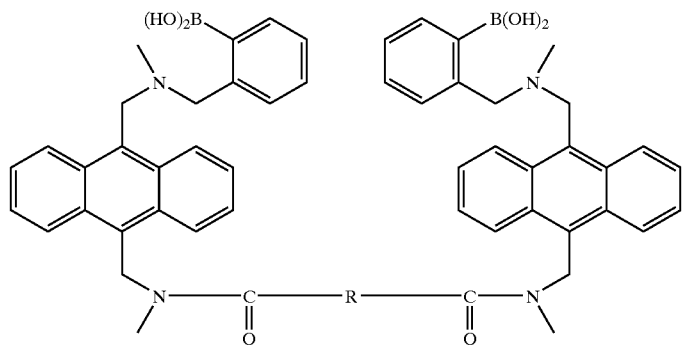
| compounds | R |
|---|---|
| 7o | -C6H4-C6H4- (4,4'-biphenyl) |
| 7p | —(CH$_2$)$_5$— |
| 7q | -C6H4- (1,4-phenylene) |
| 7r | -C6H4-O-C6H4- |
| 7s | cyclohexane-1,4-diyl |
| 7t | cyclohexane-1,4-diyl |
| 7u | naphthalene-2,6-diyl |
| 7v | thiophene-2,5-diyl |
| 7w | pyridine-3,5-diyl |
| 7x | —(CH$_2$)$_{14}$— |
| 7y | —(CH$_2$)$_4$— |
| 7z | naphthalene-1,4-diyl |

The compounds of the invention are useful for selectively binding and thus detecting saccharides. In preferred embodiments, the chemical structure of the compounds is such that they selectively bind a target saccharide because they form complexes with that saccharide that have a higher stability constant than complexes formed with other saccharides. Although not desiring to be bound to any particular theory of the invention. this selectivity is accomplished by providing diboronic acid compounds and systems that control saccharide selectivity through two point binding to diol moieties present on the saccharide. The terms "selectively bind" or "preferentially bind," as used herein, means that the fluorescent compound has a sufficiently higher affinity for the target saccharide analyte than to other molecules of similar concentration contained in the same sample volume. The affinity is sufficiently higher if the signal due to the binding of other molecules to the sensor compound is negligible compared to the binding of the sensor to the target analyte. For example, compound 7b of the present invention (see Table 1) is stated to "selectively bind" to glucose as opposed to fructose in that it binds with a higher affinity to its target saccharide, glucose, and has negligible if any binding to a non-target saccharide, fructose.

In one embodiment of the present invention, the compound of the present invention referred to herein as 7b (Table 1) selectively binds the monosaccharide glucose. In an alternative embodiment of the invention, the compound referred to herein as 7q (Table 1) selectively binds sialyl Lewis X.

Although each fluorescent sensor compound of the present invention contains a fluorophore in its molecular structure, it does not emit fluorescence in the absence of its target saccharide analyte. As explained above, with PET sensor molecules, the fluorescence of the fluorophore is quenched by the unshared electron pair of the nitrogen atom(s). When the sensor compound binds the saccharide analyte contained in a sample, the unshared electron pair of the nitrogen atom participates in the formation of an intramolecular complex of the sensor compound and the analyte. Consequently, the intrinsic fluorescence of the sensor becomes expressed.

Fluorescent signals generated when the compounds of the present invention bind a saccharide may be detected and measured in units of intensity, emission wavelength, fluorescence lifetime, polarization, phase, or combinations thereof. The amount of signal generated by the binding of the sensor compound to the target saccharide can be correlated to the concentration by methods that will be known to the skilled artisan. For example, the artisan may determine the concentration of the analyte in a sample by comparing the signal generated with a reference measurement, wherein the reference measurement is the amount of signal generated when the compound is bound to a known quantity of the target saccharide analyte.

The detection with the fluorescent compound of the present invention may be performed by adding the fluorescent compound to a sample and then, using a photoscopic method, determining the increased intensity of the fluorescence due to the binding of the compound with the saccharide. Alternatively, the detection with the fluorescent compound of the present invention may be conducted by a chromatographic method where the compound of the present invention is supported on a supporting material through which the saccharide-containing sample is passed. In the detection of a specific saccharide from a sample which may contain plural saccharides, the sample may be and preferably is subject to a pretreatment (e.g., chromatography) for the separation of the saccharides, followed by detection with the fluorescent compound of the present invention.

Compounds of the present invention may be used to detect saccharides in biological samples. As used herein, the term "biological sample" is intended to include biological samples in solid form and biological samples in fluid form. Biological samples may be obtained from the bodies of healthy subjects, or from subjects with frank or occult disease. Exemplary biological samples in fluid form include, but are not limited to, urine, whole blood, plasma, serum, sputum, saliva, sweat, interstitial fluid, cerebral spinal fluid, and dialysate obtained in kidney dialysis, and the like. Exemplary biological samples in solid form include, but are not limited to tissue samples, internal organs, biopsies, tissue, skin, stool, swabbings from mucocutaneous membranes, and so forth.

Biological samples may be taken from animal or human subjects, with humans being exemplary subjects. Exemplary animals include vertebrates such as livestock (e.g., cows, pigs, horses, sheep, chickens), laboratory animals (e.g., rats, mice, rabbits, monkeys), and pet animals such as dogs, cats, guinea pigs, etc.

As set forth herein, compounds of the present invention may be used to detect cells that are associated with cancer, and in particular, hepatocellular carcinoma. In particular, the compounds of the present invention are used to detect cells that express cell-surface polysaccharides, where the expression of such saccharides on the cell is associated with the onset, or risk or actual presence of cancer. Such polysaccharides include sialyl Lewis X and Lewis Y (see FIG. 1). The term "cancer" as used herein refers to any type of cancer, particularly solid tumors and preferably carcinomas. Specific cancers that may be detected by the methods of the invention include colon, pancreatic, ovarian, gastric, breast, lung, hepatocellular, prostate, bladder, renal cell, and uterine cancer. In an exemplary embodiment of the invention, hepatocellular carcinoma cancer cells that express sialyl Lewis X on their surfaces are detected.

The fluorescent sensor compounds of the present invention may be used in both homogeneous and heterogeneous binding assay formats, and can be easily attached to solid surfaces. Consequently, the sensor compounds are well suited for applications in particle-based assays and flow cytometry assays. Numerous particle based assays and flow cytometry assays are known in the art.

In a particle-based assay, fluorescent sensor compounds of the invention are either attached to the surface or incorporated into the body of a solid particles. The solid substrate may be a micro particle, ranging, for example from about 0.1 to about 20 micrometers. The particles are preferably round and uniform, such as commonly available polystyrene latex particles formed by emulsion polymerization. They may be produced of other materials and by other processes that are known in the art. Examples of the materials and methods include, but are not limited to, plasticized polyvinyl chloride (PVC) particles produced by droplet casting of dissolved polymers or glass-like particles produced from sol gels. In addition, the particles may be made of a bio-resorbable polymer. Examples of a bio-resorbable polymer include, but are not limited to, polyglycolic acid (PGA), poly-DL-lactide-co-glycolide (PLGA), starch, gelatin, and the like. Solid particles may be hydrophilic particles such as, but not limited to, controlled pore glass (CPG) beads or a polymer gel. Alternatively, they may comprise semipermeable membranes such as, but not limited to, a liposomes.

In certain embodiments, such as when the detection of glucose levels is desired, the fluorescent sensor compounds of the invention may be immobilized in a saccharide-permeable biocompatible polymer matrix to form an implantable sensor. Suitable biocompatible polymer matrices used for medical implants are known in the art. The fluorescent sensor compounds may be covalently bound to the polymer matrix using techniques such as those described in U.S. Pat. No. 6,002,954, which is hereby incorporated by reference. Such methods generally involve adding a suitable tether to the molecule such that the tether can be used to covalently attach the compound to the matrix.

A number of implantable sensors that employ saccharide-sensing molecules (usually, glucose-sensing molecules) are known in the art and can be adapted for use with the compounds described herein. For example, U.S. Pat. No. 5,628,310 to Rao et al., which is incorporated herein by reference, describes an apparatus and method to enable minimally invasive transdermal measurements of the fluorescence lifetime of an implanted element. U.S. Pat. No. 5,476,094 to Allen et al., which is incorporated herein by reference, describes membranes that are useful in the fabrication of biosensors, e.g., a glucose sensor, intended for in vivo use. U.S. Pat. No. 6,040,194 to Chick et al., which is incorporated herein by reference, discloses in vivo methods and apparatuses for detecting an analyte such as glucose in an individual. U.S. Pat. Nos. 6,011,984 and 6,319,540 to Van Antwerp et al., which are incorporated herein by reference, disclose methods for the determination of the concentration of biological levels of polyhydroxylated compounds, particularly glucose. These methods utilize an amplification system that is an analyte transducer immobilized in a polymeric matrix, where the system is implantable and biocompatible. Upon interrogation by an optical system, the amplification system produces a signal capable of detection external to the skin of the patient. Quantitation of the analyte of interest is achieved by measurement of the emitted signal.

Once implanted, the sensor devices can remain in place for long periods in time, with the target saccharide (i.e., glucose) being measured through the skin by optical excitation and detection.

In a typical implantable glucose sensor for use with the present invention, fluorescent sensor compounds are incorporated into the matrix to form a small sensor. The sensor may be implanted into the body of a subject, for example about 1–3 mm below the skin surface. The sensor is interrogated by an external instrument that contains a light source to excite the fluorescence, and a detector to measure the resultant emission. The detected optical signals are then converted into a glucose concentration. In general, a calibration method will be required. For example, fluorescent lifetime measurement techniques may be used; alternatively, ratiometric methods using a second glucose insensitive fluorophore contained within the polymer may be used.

U.S. Pat. No. 6,355,793 to Bell et al., incorporated herein by reference, describes a minimally invasive method of glucose monitoring in which a sensor particle (such as a hydrophilic particle such as pore glass or polymer gel or bead, or semipermeable membrane) is placed into a subject's body, where the particle is in contact with interstitial fluid in the body (e.g., under the skin). The sensor comprises a compound that generates a signal in response to the presence of the glucose, which signal can be detected. Sensor particles may be placed into the skin or under the skin. The particle comprises a compound that undergoes a photo-induced electron transfer (PET) in response to binding with a target analyte such as glucose. Accordingly, the fluorescent sensor compounds of the present invention may be used in conjunction with this method.

EXAMPLES

The following Examples have been included to illustrate modes of the invention. Certain aspects of the following Examples are described in terms of techniques and procedures found or contemplated by the present co-inventors to work well in the practice of the invention. These Examples illustrate standard laboratory practices of the co-inventors. In light of the present disclosure and the general level of skill in the art, those of skill will appreciate that the following Examples are intended to be exemplary only and that numerous changes, modifications, and alterations can be employed without departing from the scope of the invention.

In the following Examples, chemical structures referred to by number correspond to the similarly labeled compounds of Scheme 1, shown in FIG. 3, and in Table 1, above.

Example 1

General Chemistry

All $^1$H and $^{13}$C NMR spectra were recorded at 300 MHz and 75 MHz, respectively with tetramethylsilane as the internal standard. Column chromatography was performed using silica gel (200–400 mesh) from Aldrich and neutral activated Brockmann I aluminum oxide (~150 mesh) from EM Science. Elemental analyses were performed by Atlantic Microlab Inc., Norcross, Ga. Mass spectral analyses were performed by the North Carolina State University Mass Spectrometry Facility and the University of Kansas Mass Spectrometry Laboratory. IR spectra were recorded on a Perkin-Elmer 1600 series spectrometer. Tetrahydrofuran (THF) was distilled from Na and benzophenone. Acetonitrile ($CH_3CN$) and dichloromethane ($CH_2Cl_2$) were distilled from $CaH_2$. All pH values were determined with an Accumet 1003 Handhold pH/mV/Ion Meter (Fisher Scientific). A Shimadzu RF-5301 PC fluorimeter was used for the fluorescence studies. The excitation wavelength was set at 370 nm.

(10-Methylaminomethyl-anthracen-9-yl)-methanol (2). To the solution of compound 1 (2.00 g, 8.47 mmol) in MeOH (100 mL) and THF (50 mL) was added the aqueous solution of methylamine (40%, wt, 20 mL). The resulting mixture was stirred at room temperature under nitrogen for 16 h and then sodium borohydride (0.90 g, 23.7 mmol) was added and kept stirring for 30 min. After solvent evaporation, the resulting solid was dissolved in the mixture of ethyl acetate (100 mL) and water (50 mL). The organic phase was separated, and dried over $MgSO_4$. Solvent evaporation gave a crude product, which was purified on a silica gel column, eluting with $MeOH/CH_2Cl_2$ (1/50), to give compound 2 as a yellow solid (1.91 g, 90%). $^1$H NMR ($CDCl_3$) δ 8.45–8.42 (m, 2H), 8.37–8.34 (m, 2H), 7.55–7.52 (m, 4H), 5.64 (s, 2H), 4.65 (s, 2H), 2.65 (s, 3H). $^{13}$C NMR ($CDCl_3$) δ 133.4, 131.7, 130.4, 130.3, 126.2, 126.1, 125.1, 124.8, 57.7, 48.2, 37.3. HRMS (FAB) calcd for $C_{17}H_{18}NO$ ($M^++H$) 252.1388, found 252.1373. Anal. calcd for $C_{17}H_{17}NO$: C, 81.24; H, 6.82; N, 5.57. Found: C, 80.96; H, 6.86; N, 5.53.

(10-Hydroxymethyl-anthracen-9-ylmethyl)-methyl-carbamic acid tert-butyl ester (3). Compound 2 (2.10 g, 8.37 mmol), di-tert-butyl dicarbonate (3.80 g, 17.4 mmol) and trimethylamine (20 mL) were mixed in MeOH (120 mL), and then stirred at room temperature for 30 min. After removal of the solvent, the resulting residue was dissolved in ethyl acetate (100 mL), washed with water (3×50 mL), 10% aqueous solution of sodium carbonate (30 mL) and saturated brine (50 mL) and dried over $MgSO_4$. Solvent evaporation gave a crude product, which was purified on a silica gel column, eluting with ethyl acetate/hexanes (1/50–1/2), giving compound 3 as a yellow solid (2.30 g, 78%). $^1$H NMR ($CDCl_3$) δ 8.51–8.43 (m, 4H), 7.60–7.55 (m, 4H), 5.71 (d, J=5.6 Hz, 2H), 5.50 (s, 2H), 2.47 (s, 3H), 1.55 (s, 9H). $^{13}$C NMR ($CDCl_3$) δ 156.0, 132.6, 131.3, 130.2, 129.9, 126.1, 125.8, 125.4, 125.0, 80.1, 57.6, 42.7, 31.8, 28.7. IR (cm$^{-1}$): 3413, 1681. HRMS (FAB) calcd for C$_{22}$H$_{25}$NO$_3$ (M$^+$) 351.1834, found 351.1835. Anal. calcd for C$_{22}$H$_{25}$NO$_3$: C, 75.19; H, 7.17; N, 3.99. Found: C, 75.21; H, 7.27; N, 3.97.

(10-Formyl-anthracen-9-ylmethyl)-methyl-carbamic acid tert-butyl ester (4). Compound 3 (2.30 g, 6.55 mmol) was dissolved in the mixture of dry DMSO (20 mL) and trimethylamine (20 mL). To the solution thus prepared was added the solution of pyridine sulfur trioxide (7.30 g, 45.9 mmol) dissolved in dry DMSO (20 mL) over a period of 30 min. The reaction mixture was stirred at room temperature under nitrogen for 30 min, and then poured into ice-water (300 mL), extracted with ethyl acetate (3×100 mL), dried over MgSO$_4$. Solvent evaporation gave a yellow solid (2.30 g, 100%), without further purification. $^1$H NMR (CDCl$_3$) δ 11.51 (s, 1H), 8.90 (d, J=8.5 Hz, 2H), 8.51 (d, J=8.5 Hz, 2H), 7.70–7.61 (m, 4H), 5.56 (s, 2H), 2.48 (s, 3H), 1.56 (s, 9H).

Methyl-(10-methylaminomethyl-anthracen-9-ylmethyl)-carbamic acid tert-butyl ester (5). Compound 4 (2.29 g, 6.56 mmol) was dissolved in the mixture of THF (50 mL) and MeOH (50 mL). To this solution was added the aqueous solution of methylamine (40%, wt, 20 mL), the reaction mixture was stirred at room temperature under nitrogen for 12 h. Sodium borohydride (1.00 g, 26.3 mmol) was added, and stirred for 30 min. After removal of the solvent in vacuo, the resulting residue was dissolved in ethyl acetate (100 mL), washed with water (3×50 mL), and dried over MgSO$_4$. Solvent evaporation gave a crude product, which was purified on a silica gel column, eluting with MeOH/CH$_2$Cl$_2$ (1/2), giving compound 5 as a yellow solid (2.00 g, 83%). $^1$H NMR (CDCl$_3$) δ 8.44–8.39 (m, 4H), 7.56–7.53 (m, 4H), 5.51 (s, 2H), 4.71 (s, 2H), 2.69 (s, 3H), 2.46 (s, 3H), 1.55 (s, 9H). $^{13}$C NMR (CDCl$_3$) δ 155.6, 132.5, 131.0, 130.0, 125.8, 125.7, 125.4, 125.3, 124.9, 79.7, 47.8, 42.6, 36.9, 31.6, 28.6. IR (cm$^{-1}$): 1686. HRMS (FAB) calcd for C$_{23}$H$_{28}$N$_2$O$_2$ (M$^+$) 364.2151, found 364.2159. Anal. calcd for C$_{23}$H$_{28}$N$_2$O$_2$: C, 75.79; H, 7.74; N, 7.69. Found: C, 75.64; H, 7.71; N, 7.53.

Example 2

General Procedures for Preparation of Boc-Protected Diamines (6)

The di-acid (0.138 mmol, 0.5 equiv.) was dissolved in dry CH$_2$Cl$_2$ (20 mL), then 1-(2-dimethylaminopropyl)-3-ethylcarbodiimide hydrochloride (EDC, 210 mg, 1.10 mmol, 4.0 equiv.) was added. To this solution was added compound 5 (100 mg, 0.275 mmol, 1.0 equiv.). The reaction mixture was stirred at room temperature under nitrogen for 12 h, then washed with water (2×30 mL), and dried over MgSO$_4$. After solvent evaporation, the crude product was purified on a silica gel column, eluting with MeOH/CH$_2$Cl$_2$ to give the product.

[10-({[11-({10-[(tert-Butoxycarbonyl-methyl-amino)-methyl]-anthracen-9-ylmethyl}-methyl-carbamoyl)-undecanoyl]-methyl-amino}-methyl)-anthracen-9-ylmethyl]-methyl-carbamic acid tert-butyl ester (6a). Yield 52%. $^1$H NMR (CDCl$_3$) δ 8.49–8.46 (m, 4H), 8.40–8.37 (m, 4H), 7.59–7.54 (m, 8H), 5.71 (s, 4H), 5.54 (s, 4H), 2.60 (s, 6H), 2.49 (s, 6H), 2.40–2.35 (m, 4H), 1.72–1.55 (m, 22H), 1.36–1.31 (m, 12H). IR (cm$^{-1}$): 1684, 1637. HRMS (FAB) calcd for C$_{58}$H$_{75}$N$_4$O$_6$ (M$^+$+H) 923.5687, found 923.5716.

(10-{[(2-{2-[({10-[(tert-Butoxycarbonyl-methyl-amino)-methyl]-anthracen-9-ylmethyl}-methyl-carbamoyl)-methyl]-phenyl}-acetyl)-methyl-amino]-methyl}-anthracen-9-ylmethyl)-methyl-carbamic acid tert-butyl ester (6b). Yield 88%. $^1$H NMR (CDCl$_3$) δ 8.47–8.39 (m, 8H), 7.53–7.49 (m, 8H), 7.26 (d, J=4.2 Hz, 4H), 5.74 (s, 4H), 5.53 (s, 4H), 3.81 (s, 4H), 2.62 (s, 6H), 2.45 (s, 6H), 1.56 (s, 18H). IR (cm$^{-1}$): 1684, 1643. HRMS (FAB) calcd for C$_{56}$H$_{63}$N$_4$O$_6$ (M$^+$+H) 887.4748, found 887.4733.

(10-{[(2-{2-[({10-[(tert-Butoxycarbonyl-methyl-amino)-methyl]-anthracen-9-ylmethyl}-methyl-carbamoyl)-methoxy]-phenoxy}-acetyl)-methyl-amino]-methyl}-anthracen-9-ylmethyl)-methyl-carbamic acid tert-butyl ester (6c). Yield 44%. $^1$H NMR (CDCl$_3$) δ 8.47 (d, J=9.0 Hz, 4H), 8.33 (d, J=9.0 Hz, 4H), 7.54–7.49 (m, 8H), 7.0 (s, 4H), 5.69 (s, 4H), 5.51 (s, 4H), 4.79 (s, 4H), 2.60 (s, 6H), 2.47 (s, 6H), 1.60 (s, 18H). IR (cm$^{-1}$): 1672. HRMS (FAB) calcd for C$_{56}$H$_{63}$N$_4$O$_8$ (M$^+$+H) 919.4646, found 919.4681.

(10-{[(3-{4-[2-({10-[(tert-Butoxycarbonyl-methyl-amino)-methyl]-anthracen-9-ylmethyl}-methyl-carbamoyl)-ethyl]-phenyl}-propionyl)-methyl-amino]-methyl-}-anthracen-9-ylmethyl)-methyl-carbamic acid tert-butyl ester (6d). Yield 73%. $^1$H NMR (CDCl$_3$) δ 8.48–8.45 (m, 4H), 8.38–8.35 (m, 4H), 7.57–7.54 (m, 8H), 7.18 (s, 4H), 5.71 (s, 4H), 5.53 (s, 4H), 3.06 (t, J=8.7 Hz, 4H), 2.65 (t, J=8.7 Hz, 4H), 2.53 (s, 6H), 2.48 (s, 6H), 1.56 (s, 18H). IR (cm$^{-1}$): 1684, 1643. HRMS (FAB) calcd for C$_{58}$H$_{67}$N$_4$O$_6$ (M$^+$+H) 915.5061 found 915.5070.

[10-({[4-({10-[(tert-Butoxycarbonyl-methyl-amino)-methyl]-anthracen-9-ylmethyl}-methyl-carbamoyl)-butyryl]-methyl-amino}-methyl)-anthracen-9-ylmethyl]-methyl-carbamic acid tert-butyl ester (6e). Yield 53%. $^1$H NMR (CDCl$_3$) δ 8.48–8.45 (m, 4H), 8.39–8.35 (m, 4H), 7.55–7.52 (m, 8H), 5.69 (s, 4H), 5.54 (s, 4H), 2.63 (s, 6H), 2.54 (t, J=7.0 Hz, 4H), 2.48 (s, 6H), 2.20–2.10 (m, 2H), 1.57 (s, 18H). IR (cm$^{-1}$): 1685, 1639. HRMS (FAB) calcd for C$_{51}$H$_{61}$N$_4$O$_6$ (M$^+$+H) 825.4591, found 825.4627. Anal. calcd for C$_{51}$H$_{60}$N$_4$O$_6$1.5H$_2$O: C, 71.82; H, 7.39; N, 6.57. Found: C, 71.93; H, 7.43; N, 6.27.

[10-({[2-({10-[(tert-Butoxycarbonyl-methyl-amino)-methyl]-anthracen-9-ylmethyl}-methyl-carbamoyl)-benzoyl]-methyl-amino}-methyl)-anthracen-9-ylmethyl]-methyl-carbamic acid tert-butyl ester (6f). Yield 64%. $^1$H NMR (CDCl$_3$) δ 8.58–8.51 (m, 8H), 7.67–7.60 (m, 8H), 7.29–7.26 (m, 2H), 7.08 (m, 2H), 5.94 (s, 4H), 5.58 (s, 4H), 2.67 (s, 6H), 2.53 (s, 6H), 1.57 (s, 18H). IR (cm$^{-1}$): 1680, 1633. HRMS (FAB) calcd for C$_{54}$H$_{59}$N$_4$O$_6$ (M$^+$+H) 859.4435, found 859.4449. Anal. calcd for C$_{54}$H$_{58}$N$_4$O$_6$.1.5H$_2$O: C, 73.13; H, 6.88; N, 6.32. Found: C, 73.02; H, 6.68; N, 6.21.

[10-({[5-({10-[(tert-Butoxycarbonyl-methyl-amino)-methyl]-anthracen-9-ylmethyl}-methyl-carbamoyl)-pent-3-enoyl]-methyl-amino}-methyl)-anthracen-9-ylmethyl]-methyl-carbamic acid tert-butyl ester (6g). Yield 31%. $^1$H NMR (CDCl$_3$) δ 8.46–8.43 (m, 4H), 8.36–8.32 (m, 4H), 7.59–7.56 (m, 8H), 5.79 (s, 2H), 5.68 (s, 4H), 5.52 (s, 4H), 3.24 (s, 4H), 2.56 (s, 6H), 2.48 (s, 6H), 1.56 (s, 18H). IR (cm$^{-1}$): 1689, 1642. HRMS (FAB) calcd for C$_{52}$H$_{61}$N$_4$O$_6$ (M$^+$+H) 837.4591, found 837.4592. Anal. calcd for C$_{52}$H$_{60}$N$_4$O$_6$.2H$_2$O: C, 71.55; H, 7.33; N, 6.42. Found: C, 71.70; H, 7.03; N, 6.31.

[10-({[3-({10-[(tert-Butoxycarbonyl-methyl-amino)-methyl]-anthracen-9-ylmethyl}-methyl-carbamoyl)-propionyl]-methyl-amino}-methyl)-anthracen-9-ylmethyl]-methyl-carbamic acid tert-butyl ester (6h). Yield 78%. $^1$H NMR (CDCl$_3$) δ 8.48–8.41 (m, 8H), 7.60–7.55 (m, 8H), 5.77 (s, 4H), 5.56 (s, 4H), 2.86 (s, 4H), 2.79 (s, 6H), 2.50 (s, 6H), 1.53 (s, 18H). IR (cm$^{-1}$): 1685, 1643. HRMS (FAB) calcd for C$_{50}$H$_{59}$N$_4$O$_6$ (M$^+$+H) 811.4356, found 811.4412. Anal. calcd for C$_{50}$H$_{58}$N$_4$O$_6$: C, 74.05; H, 7.21; N, 6.91. Found: C, 74.01; H, 7.34; N, 6.63.

[10-({[7-({10-[(tert-Butoxycarbonyl-methyl-amino)-methyl]-anthracen-9-ylmethyl}-methyl-carbamoyl)-heptanoyl]-methyl-amino}-methyl)-anthracen-9-ylmethyl]-methyl-carbamic acid tert-butyl ester (6i). Yield 75%. $^1$H NMR (CDCl$_3$) δ 8.49–8.38 (m, 8H), 7.58–7.55 (m, 8H), 5.71 (s, 4H), 5.54 (s, 4H), 2.60 (s, 6H), 2.50 (s, 6H), 2.39 (t, J=1.5 Hz, 4H), 1.90–1.40 (m, 8H), 1.58 (s, 18H). IR (cm$^{-1}$): 1684, 1636. HRMS (FAB) calcd for C$_{54}$H$_{69}$N$_4$O$_6$ (M$^+$+H) 867.4982, found 867.5229.

[10-({[21-({10-[(tert-Butoxycarbonyl-methyl-amino)-methyl]-anthracen-9-ylmethyl}-methyl-carbamoyl)-heneicosanoyl]-methyl-amino}-methyl)-anthracen-9-ylmethyl]-methyl-carbamic acid tert-butyl ester (6j). Yield 64%. $^1$H NMR (CDCl$_3$) δ 8.49–8.38 (m, 8H), 7.59–7.56 (m, 8H), 5.72 (s, 4H), 5.55 (s, 4H), 2.60 (s, 6H), 2.50 (s, 6H), 2.40–2.34 (m, 4H), 1.90–1.20 (m, 54H). IR (cm$^{-1}$): 1692, 1643. HRMS (FAB) calcd for C$_{68}$H$_{95}$N$_4$O$_6$ (M$^+$+H), 1063.7173, found 1063.5746. Anal. calcd for C$_{54}$H$_{58}$N$_4$O$_6$.0.5H$_2$O: C, 72.15; H, 8.92; N, 5.22. Found: C, 76.15; H, 8.92; N, 4.76.

[10-({[3-({10-[(tert-Butoxycarbonyl-methyl-amino)-methyl]-anthracen-9-ylmethyl}-methyl-carbamoyl)-benzoyl]-methyl-amino}-methyl)-anthracen-9-ylmethyl]-methyl-carbamic acid tert-butyl ester (6k). Yield 74%. $^1$H NMR (CDCl$_3$) δ 8.52–8.45 (m, 8H), 7.60–7.56 (m, 8H), 7.50–7.40 (m, 4H), 5.85 (s, 4H), 5.58 (s, 4H), 2.53 (s, 12H), 1.59 (s, 18H). IR (cm$^{-1}$): 1688, 1632. HRMS (FAB) calcd for C$_{54}$H$_{59}$N$_4$O$_6$ (M$^+$+H) 859.4435, found 859.4832. Anal. calcd for C$_{54}$H$_{58}$N$_4$O$_6$.1.5H$_2$O: C, 73.20; H, 6.88; N, 6.32. Found: C, 73.46; H, 6.93; N, 6.05.

{10-[({4-[({10-[(Isopropoxycarbonyl-methyl-amino)-methyl]-anthracen-9-ylmethyl}-methyl-carbamoyl)-methoxy]-benzoyl}-methyl-amino)-methyl]-anthracen-9-ylmethyl}-methyl-carbamic acid tert-butyl ester (6l). Yield 60%. $^1$H NMR (CDCl$_3$) δ 8.50–8.31 (m, 8H), 7.62–7.43 (m, 10H), 6.99–6.96 (m, 2H), 5.86 (s, 2H), 5.72 (s, 2H), 5.58–5.54 (m, 4H), 4.79 (s, 2H), 2.65 (s, 3H), 2.62 (s, 3H), 2.53 (s, 3H), 2.49 (s, 3H), 1.58 (s, 18H). IR (cm$^{-1}$): 1682, 1626. HRMS (FAB) calcd for C$_{55}$H$_{61}$N$_4$O$_7$ (M$^+$+H) 889.4462, found 889.4086. Anal. calcd for C$_{52}$H$_{60}$N$_4$O$_7$.H$_2$O: C, 73.56; H, 6.85; N, 6.23. Found: C, 73.31; H, 7.50; N, 5.35.

[10-({[13-({10-[(tert-Butoxycarbonyl-methyl-amino)-methyl]-anthracen-9-ylmethyl}-methyl-carbamoyl)-tridecanoyl]-methyl-amino}-methyl)-anthracen-9-ylmethyl]-methyl-carbamic acid tert-butyl ester (6m). Yield 52%. $^1$H NMR (CDCl$_3$) δ 8.60–8.36 (m, 8H), 7.64–7.46 (m, 8H), 5.72 (s, 4H), 5.55 (s, 4H), 2.60 (s, 6H), 2.50 (s, 6H), 2.42–2.32 (m, 4H), 1.92–1.20 (m, 20H), 1.56 (s, 18H). HRMS (FAB) calcd for C$_{60}$H$_{79}$N$_4$O$_6$ (M$^+$+H) 951.6000, found 951.6009. Anal. calcd. for C$_{60}$H$_{78}$N$_4$O$_6$: C, 75.75; H, 8.26; N, 5.89. Found: C, 75.55; H, 8.37; N, 5.75.

[10-({[2'-({10-[(tert-Butoxycarbonyl-methyl-amino)-methyl]-anthracen-9-ylmethyl}-methyl-carbamoyl)-biphenyl-2-carbonyl]-methyl-amino}-methyl)-anthracen-9-ylmethyl]-methyl-carbamic acid tert-butyl ester (6n). Yield 59%. $^1$H NMR (CDCl$_3$) δ 8.54–8.20 (m, 8H), 7.64–7.44 (m, 8H), 7.42–7.20 (m, 8H), 5.51 (s, 8H), 5.51 (s, 8H), 2.47 (s, 12H), 1.57 (s, 18H). HRMS (FAB) calcd for C$_{60}$H$_{63}$N$_4$O$_6$ (M$^+$+H) 935.4748, found 935.4770. Anal. calcd. for C$_{60}$H$_{62}$N$_4$O$_6$.0.5H$_2$O: C, 76.32; H, 6.72; N, 5.93. Found: C, 76.57; H, 7.09; N, 5.65.

[10-({[4'-({10-[(tert-Butoxycarbonyl-methyl-amino)-methyl]-anthracen-9-ylmethyl}-methyl-carbamoyl)-biphenyl-4-carbonyl]-methyl-amino}-methyl)-anthracen-9-ylmethyl]-methyl-carbamic acid tert-butyl ester (6o). Yield 62%. $^1$H NMR (CDCl$_3$) δ 8.40–8.20 (m, 8H), 7.80–7.40 (m, 16H), 5.90 (s, 4H), 5.57 (s, 4H), 2.60 (s, 6H), 2.52 (s, 6H), 1.58 (s, 18H). HRMS (FAB) calcd for C$_{60}$H$_{63}$N$_4$O$_6$ (M$^+$+H) 935.4748, found 935.4775. Anal. calcd. for C$_{60}$H$_{62}$N$_4$O$_6$.0.5H$_2$O: C, 76.32; H, 6.72; N, 5.93. Found: C, 76.29; H, 6.68; N, 5.94.

[10-({[6-({10-[(tert-Butoxycarbonyl-methyl-amino)-methyl]-anthracen-9-ylmethyl}-methyl-carbamoyl)-hexanoyl]-methyl-amino}-methyl)-anthracen-9-ylmethyl]-methyl-carbamic acid tert-butyl ester (6p). Yield 56%. $^1$H NMR (CDCl$_3$) δ 8.52–8.36 (m, 8H), 7.64–7.54 (m, 8H), 5.71 (s, 4H), 5.54 (s, 4H), 2.60 (s, 6H), 2.49 (s, 6H), 2.41 (t, J=7.5 Hz, 4H), 1.90–1.20 (m, 6H), 1.57 (s, 18H). IR (cm$^{-1}$): 1683, 1635. HRMS (FAB) calcd for C$_{53}$H$_{65}$N$_4$O$_6$ (M$^+$+H) 853.4904; found 853.4916.

[10-({[4-({10-[(tert-Butoxycarbonyl-methyl-amino)-methyl]-anthracen-9-ylmethyl}-methyl-carbamoyl)-benzoyl]-methyl-amino}-methyl)-anthracen-9-ylmethyl]-methyl-carbamic acid tert-butyl ester (6q). Yield 57%. $^1$H NMR (CDCl$_3$) δ 8.60–8.40 (m, 8H), 7.63–7.55 (m, 8H), 7.40 (s, 4H), 5.86 (s, 4H), 5.55 (s, 4H), 2.51 (s, 12H), 1.62 (s, 18H). IR (cm$^{-1}$): 1684, 1635. HRMS (FAB) calcd for C$_{54}$H$_{59}$N$_4$O$_6$ (M$^+$+H) 859.4435; found 859.4451.

{10-[({4-[4-({10-[(tert-Butoxycarbonyl-methyl-amino)-methyl]-anthracen-9-ylmethyl}-methyl-carbamoyl)-phenoxy]-benzoyl}-methyl-amino)-methyl]-anthracen-9-ylmethyl}-methyl-carbamic acid tert-butyl ester (6r). Yield 79%. $^1$H NMR (CDCl$_3$) δ 8.60–8.40 (m, 8H), 7.70–7.50 (m, 8H), 7.49–7.39 (m, 4H), 7.09–6.99 (m, 4H), 5.84 (s, 4H), 5.55 (s, 4H), 2.58 (s, 6H), 2.40 (s, 6H), 1.57 (s, 18H). IR (cm$^{-1}$): 1682, 1632. HRMS (FAB) calcd for C$_{60}$H$_{63}$N$_4$O$_7$ (M$^+$+H) 951.4697; found 951.4684.

[10-({[4-({10-[(tert-Butoxycarbonyl-methyl-amino)-methyl]-anthracen-9-ylmethyl}-methyl-carbamoyl)-cyclohexanecarbonyl]-methyl-amino}-methyl)-anthracen-9-ylmethyl]-methyl-carbamic acid tert-butyl ester (6s). Yield 83%. $^1$H NMR (CDCl$_3$) δ 8.60–8.40 (m, 4H), 8.38–7.22 (m, 4H), 7.70–7.50 (m, 8H), 5.72 (s, 4H), 5.55 (s, 4H), 2.66 (s, 6H), 2.45 (s, 6H), 1.90–1.86 (m, 4H), 1.77–1.50 (m, 4H), 1.55 (s, 18H). IR (cm$^{-1}$): 1682, 1634. HRMS (FAB) calcd for C$_{54}$H$_{63}$N$_4$O$_6$ (M$^+$+H) 865.4904; found 865.4886.

[10-({[4-({10-[(tert-Butoxycarbonyl-methyl-amino)-methyl]-anthracen-9-ylmethyl}-methyl-carbamoyl)-cyclohexanecarbonyl]-methyl-amino}-methyl)-anthracen-9-ylmethyl]-methyl-carbamic acid tert-butyl ester (6t). Yield 83%. $^1$H NMR (CDCl$_3$) δ 8.60–8.40 (m, 8H), 7.70–7.50 (m, 8H), 5.77 (s, 4H), 5.56 (s, 4H), 2.70 (s, 6H), 2.55 (s, 6H), 2.56–2.22 (m, 4H), 1.48 (s, 18H), 1.40–1.20 (m, 4H). IR (cm$^{-1}$): 1686, 1637. HRMS (FAB) calcd for C$_{54}$H$_{65}$N$_4$O$_6$ (M$^+$+H) 865.4904; found 865.4886.

[10-({[6-({10-[(tert-Butoxycarbonyl-methyl-amino)-methyl]-anthracen-9-ylmethyl}-methyl-carbamoyl)-naphthalene-2-carbonyl]-methyl-amino}-methyl)-anthracen-9-ylmethyl]-methyl-carbamic acid tert-butyl ester (6u). Yield 67%. $^1$H NMR (CDCl$_3$) δ 8.53–8.50 (m, 8H), 7.89–7.86 (m, 4H), 7.62–7.51 (m, 10H), 5.91 (s, 4H), 5.56 (s, 4H), 2.59 (s, 6H), 2.51 (s, 6H), 1.57 (s, 18H). IR (cm$^{-1}$): 1688, 1631. MS-FAB 909.8 (M$^+$+H).

[10-({[5-({10-[(tert-Butoxycarbonyl-methyl-amino)-methyl]-anthracen-9-ylmethyl}-methyl-carbamoyl)-thiophene-2-carbonyl]-methyl-amino}-methyl)-anthracen-9-ylmethyl]-methyl-carbamic acid tert-butyl ester (6v). Yield 55%. $^1$H NMR (CDCl$_3$) δ 8.52–8.49 (m, 4H), 8.39–8.37 (m, 4H), 7.61–7.56 (m, 8H), 7.24 (s, 2H), 5.86 (s, 4H), 5.56 (s, 4H), 2.80 (s, 6H), 2.51 (s, 6H), 1.56 (s, 18H). IR (cm$^{-1}$): 1686, 1612. HRMS (FAB) calcd for C$_{52}$H$_{57}$N$_4$O$_6$S (M$^+$+H) 865.3999, found 865.3973.

[10-({[5-({10-[(tert-Butoxycarbonyl-methyl-amino)-methyl]-anthracen-9-ylmethyl}-methyl-carbamoyl)-pyridine-3-carbonyl]-methyl-amino}-methyl)-anthracen-9-ylmethyl]-methyl-carbamic acid tert-butyl ester (6w). Yield 69%. $^1$H NMR (CDCl$_3$) δ 8.64 (s, 2H), 8.55–8.52 (m, 4H), 8.43–8.41 (m, 4H), 7.85 (s, 1H), 7.62–7.59 (m, 8H), 5.87 (s, 4H), 5.58 (s, 4H), 2.58 (s, 6H), 2.52 (s, 6H), 1.58 (s, 18H). IR (cm$^{-1}$): 1682, 1632. HRMS (FAB) calcd for C$_{53}$H$_{58}$N$_5$O$_6$ (M$^+$) 860.4387, found 860.4412.

[10-({[15-({10-[(tert-Butoxycarbonyl-methyl-amino)-methyl]-anthracen-9-ylmethyl}-methyl-carbamoyl)-pentadecanoyl]-methyl-amino}-methyl)-anthracen-9-ylmethyl]-methyl-carbamic acid tert-butyl ester (6x). Yield 63%. $^1$H NMR (CDCl$_3$) δ 8.52–8.49 (m, 4H), 8.43–8.40 (m, 4H), 7.61–7.58 (m, 8H), 5.74 (s, 4H), 5.57 (s, 4H), 2.62 (s, 6H), 2.52 (s, 6H), 2.40 (t, J=7.2 Hz, 4H), 1.75–1.58 (m, 22H), 1.36–1.29 (m, 20H). IR (cm$^{-1}$): 1688, 1641. HRMS (FAB) calcd for $C_{62}H_{83}N_4O_6$ (M$^+$+H) 979.6313, found 979.6343.

[10-({[5-({10-[(tert-Butoxycarbonyl-methyl-amino)-methyl]-anthracen-9-ylmethyl}-methyl-carbamol)-pentanoyl]-methyl-amino}-methyl)-anthracen-9-ylmethyl]-methyl-carbamic acid tert-butyl ester (6y). Yield 50%. $^1$H NMR (CDCl$_3$) δ 8.50–8.30 (m, 8H), 7.60–7.40 (m, 8H), 5.72 (s, 4H), 5.51 (s, 4H), 2.55 (s, 6H), 2.50 (s, 6H), 2.50–2.44 (m, 4H), 1.90–1.60 (m, 4H), 1.57 (s, 18H).

[10-({[4-({10-[(tert-Butoxycarbonyl-methyl-amino)-methyl]-anthracen-9-ylmethyl}-methyl-carbamoyl)-naphthalene-1-carbonyl]-methyl-amino}-methyl)-anthracen-9-ylmethyl]-methyl-carbamic acid tert-butyl ester (6z). Yield 33%. $^1$H NMR (CDCl$_3$) d 8.80–8.40 (m, 8H), 8.00–7.40 (m, 14H), 6.10 (s, 4H), 5.65 (s, 4H), 2.60 (s, 6H), 2.40 (s, 6H), 1.60 (s, 18H). HRMS (FAB) calcd for $C_{58}H_{61}N_4O_6$ (M$^+$+H) 909.4591, found 909.4583. Anal. calcd. for $C_{58}H_{60}N_4O_6$: C, 76.63; H, 6.65; N, 6.16. Found: C, 76.36; H, 6.72; N, 6.04.

Example 3

General Procedures for Preparation of Symmetrical Diboronic Acids (7)

The Boc-protected diamine compound 6 (0.073 mmol) was dissolved in dry CH$_2$Cl$_2$ (8 mL), then trifluoroacetic acid (3 mL) was added. After the mixture was stirred at room temperature for 10 min, the solvent was removed. The residue was dried in vacuo for 3 h and dissolved in dry acetonitrile (30 mL), compound 8 (85 mg, 0.30 mmol), potassium carbonate (100 mg, 0.73 mmol) and potassium iodide (2 mg) were then added. The reaction mixture was stirred at room temperature for 12 h. The insoluble materials were filtered off, the filtrate was evaporated in vacuo. The resulting residue was dissolved in CH$_2$Cl$_2$ and 10% aqueous solution of sodium bicarbonate (20 mL) and the mixture was stirred at room temperature for 1 h. The organic phase was separated and washed with water (2×30 mL), dried over MgSO$_4$. After removal of the solvent, the crystalline was precipitated from CH$_2$Cl$_2$/Et$_2$O.

Diboronic acid 7a. Yield 49%. $^1$H NMR (CD$_3$OD) δ 8.46–8.43 (m, 4H), 8.29–8.24 (m, 4H), 7.70–7.67 (m, 2H), 7.59–7.55 (m, 8H), 7.36–7.26 (m, 6H), 5.68 (s, 4H), 5.06 (s, 4H), 4.36 (s, 4H), 2.58 (s, 6H), 2.43–2.38 (m, 4H), 1.64–1.54 (m, 4H), 1.36–1.28 (m, 12H). IR (cm$^{-1}$): 1637. MS-ESI: 496.4 (M$^+$+2H)/2.

Diboronic acid 7b. Yield 81%. $^1$H NMR (CD$_3$OD+CDCl$_3$) δ 8.40–8.36 (m, 4H), 8.25–8.22 (m, 4H), 7.82–7.18 (m, 20H), 5.69 (s, 4H), 4.89 (s, 4H), 4.08 (s, 4H), 3.75 (s, 4H), 2.54 (s, 6H), 2.25 (s, 6H). IR (cm$^{-1}$): 1637. MS-ESI: 478.4 (M$^+$+2H)/2. Anal. calcd for $C_{60}H_{60}B_2N_4O_6$·2.4H$_2$O: C, 72.21; H, 6.49; N, 5.61. Found: C, 71.96; H, 6.19; N, 5.39.

Diboronic acid 7c. Yield 38%. $^1$H NMR (CD$_3$OD+CDCl$_3$) δ 8.32–8.29 (m, 4H), 8.26–8.21 (m, 4H), 7.80–7.22 (m, 16H), 7.00 (s, 4H), 5.63 (s, 4H), 4.99 (s, 4H), 4.78 (s, 4H), 4.33 (s, 4H), 2.40 (s, 6H), 2.37 (s, 6H). IR (cm$^{-1}$): 1655. MS-ESI: 494.4 (M$^+$+2H)/2.

Diboronic acid 7d. Yield 69%. $^1$H NMR (CD$_3$OD+CDCl$_3$) δ 8.35–8.32 (m, 4H), 8.25–8.22 (m, 4H), 7.67–7.65 (m, 2H), 7.55–7.52 (m, 8H), 7.35–7.25 (m, 6H), 7.11 (s, 4H), 5.63 (s, 4H), 5.01 (s, 4H), 4.28 (s, 4H), 2.96 (t, J=7.2 Hz, 4H), 2.64 (t, J=7.2 Hz, 4H), 2.37 (s, 6H), 2.33 (s, 6H). IR (cm$^{-1}$): 1637. MS-ESI: 492.4 (M$^+$+2H)/2.

Diboronic acid 7e. Yield 58%. $^1$H NMR (CD$_3$OD+CDCl$_3$) δ 8.44–8.41 (m, 4H), 8.30–8.27 (m, 4H), 7.80–7.60 (m, 2H), 7.57–7.54 (m, 8H), 7.36–7.28 (m, 6H), 5.71 (s, 4H), 5.07 (s, 4H), 4.29 (s, 4H), 2.60 (s, 6H), 2.53 (t, J=7.1 Hz, 4H), 2.39 (s, 6H), 2.15–2.10 (m, 2H). IR (cm$^{-1}$): 1632. MS-ESI: 875.7 (M$^+$–H$_2$O+H). Anal. calcd for $C_{55}H_{58}B_2N_4O_6$·H$_2$O: C, 72.53; H, 6.59; N, 6.15. Found: C, 72.19; H, 6.16; N, 5.76.

Diboronic acid 7f. Yield 32%. $^1$H NMR (CD$_3$OD+CDCl$_3$) δ 8.62–8.60 (m, 4H), 8.34–8.31 (m, 4H), 7.70–7.59 (m, 10H), 7.39–7.27 (m, 10H), 5.88 (s, 4H), 5.09 (s, 4H), 4.36 (s, 4H), 2.61 (s, 6H), 2.44 (s, 6H). IR (cm$^{-1}$): 1633. MS-ESI: 909.6 (M$^+$–H$_2$O+H). Anal. calcd for $C_{58}H_{56}B_2N_4O_6$·2H$_2$O: C, 72.36; H, 6.23; N, 5.82. Found: C, 72.26; H, 5.75; N, 5.48.

Diboronic acid 7g. Yield 71%. $^1$H NMR (CD$_3$OD+CDCl$_3$) δ 8.31–8.28 (m, 4H), 8.18–8.15 (m, 4H), 7.56–7.50 (m, 8H), 7.40–7.30 (m, 8H), 5.65 (s, 2H), 5.57 (s, 4H), 4.90 (s, 4H), 4.26 (s, 4H), 3.18 (s, 4H), 2.33 (s, 6H), 2.16 (s, 6H). IR (cm$^{-1}$): 1642. MS-ESI: 887.6 (M$^+$–H$_2$O+H). Anal. calcd for $C_{56}H_{58}B_2N_4O_6$: C, 74.34; H, 6.46; N, 6.19. Found: C, 74.38; H, 6.73; N, 6.21.

Diboronic acid 7h. Yield 50%. $^1$H NMR (CD$_3$OD+CDCl$_3$) δ 8.49–8.46 (m, 4H), 8.24–8.22 (m, 4H), 7.80–7.60 (m, 2H), 7.57–7.54 (m, 8H), 7.36–7.28 (m, 6H), 5.70 (s, 4H), 4.96 (s, 4H), 4.33 (s, 4H), 2.78(s, 4H), 2.69 (s, 6H), 2.39 (s, 6H). IR (cm$^{-1}$): 1643, 1632. MS-ESI: 861.5 (M$^+$–H$_2$O+H).

Diboronic acid 7i. Yield 49%. $^1$H NMR (CD$_3$OD+CDCl$_3$) δ 8.50–8.25 (m, 8H), 7.71–7.57 (m, 10H), 7.35–7.28 (m, 6H), 5.73 (s, 4H), 5.16 (s, 4H), 4.30 (s, 4H), 2.59 (s, 6H), 2.47 (s, 6H), 2.39 (t, J=7.3 Hz, 4H), 1.80–1.60 (m, 4H), 1.50–1.35 (m, 4H). IR (cm$^{-1}$): 1632. MS-ESI: 917.5 (M$^+$–H$_2$O+H).

Diboronic acid 7j. Yield 30%. $^1$H NMR (CD$_3$OD+CDCl$_3$) δ 8.45–8.43(m, 4H), 8.28–8.26 (m, 4H), 7.67–7.59 (m, 10H), 7.38–7.36 (m, 6H), 5.70 (s, 4H), 5.11 (s, 4H), 4.39 (s, 4H), 2.59 (s, 6H), 2.50–2.38 (m, 10H), 1.66–1.61 (m, 4H), 1.40–1.18 (m, 32H). IR (cm$^{-1}$): 1649, 1632. MS-ESI: 1113.8 (M$^+$–H$_2$O+H).

Diboronic acid 7k. Yield 50%. $^1$H NMR (CD$_3$OD+CDCl$_3$) δ 8.50–8.34 (m, 8H), 7.71–7.61 (m, 12H), 7.45–7.34 (m, 8H), 5.86 (s, 4H), 5.06 (s, 4H), 4.24 (s, 4H), 2.57 (s, 6H), 2.42 (s, 6H). IR (cm$^{-1}$): 1631, 1620. MS-ESI: 909.5 (M$^+$–H$_2$O+H).

Diboronic acid 7l. Yield 40%. $^1$H NMR (CD$_3$OD+CDCl$_3$) δ 8.46–8.30 (m, 8H), 8.29–7.56 (m, 10H), 7.28–7.26 (m, 8H), 7.10–6.90 (m, 2H), 5.89 (s, 2H), 5.76 (s, 2H), 5.16 (s, 2H), 5.12 (s, 2H), 4.90 (s, 2H), 4.38 (s, 2H), 4.35 (s, 2H), 2.68 (s, 3H), 2.63 (s, 3H), 2.46 (s, 3H), 2.42 (s, 3H). IR (cm$^{-1}$): 1632, 1608. MS-ESI: 939.5 (M$^+$–H$_2$O+H).

Diboronic acid 7m. Yield 42%. $^1$H NMR (CD$_3$OD) δ 8.50–8.38 (m, 4H), 8.32–8.24 (m, 4H), 7.74–7.64 (m, 2H), 7.62–7.54 (m, 6H), 7.40–7.20 (m, 8H), 5.68 (s, 4H), 5.06 (s, 4H), 4.37 (s, 4H), 2.58 (s, 6H), 2.50–2.34 (m, 4H), 2.46 (s, 6H), 1.70–1.48 (m, 4H), 1.40–1.20 (m, 16H). ESI-MS: 1001.7 (M$^+$–H$_2$O+H).

Diboronic acid 7n. Yield 76%. $^1$H NMR (CD$_3$OD+CDCl$_3$) δ 8.45–7.10 (m, 32H), 5.80 (s, 4H), 4.70 (s, 4H), 4.35 (s, 4H), 2.25 (s, 12H). ESI-MS: 985.6 (M$^+$–H$_2$O+H).

Diboronic acid 7o. Yield 89%. $^1$H NMR (CD$_3$OD+CDCl$_3$) δ 8.60–8.50 (m, 4H), 8.40–8.24 (m, 4H), 7.90–7.20 (m, 24H), 5.90 (s, 4H), 4.94 (s, 4H), 4.20 (s, 4H), 2.62 (s, 6H), 2.40 (s, 6H). ESI-MS: 985.6 (M$^+$–H$_2$O+H).

Diboronic acid 7p. Yield 78%. $^1$H NMR (CD$_3$OD+CDCl$_3$) δ 8.50–8.36 (m, 4H), 8.32–8.16 (m, 4H), 7.74–7.44 (m, 10H), 7.42–7.20 (m, 6H), 5.64 (s, 4H), 4.99 (s, 4H), 4.35 (s, 4H), 2.42–2.30 (m, 4H), 2.41 (s, 6H), 2.37 (s, 6H), 1.70–1.54 (m, 4H), 1.46–1.32 (m, 2H). IR (cm$^{-1}$): 1639. MS-ESI: 949.5 (M$^+$+2MeOH–2H$_2$O+H).

Diboronic acid 7q. Yield 70%. $^1$H NMR (CD$_3$OD) δ 8.60–8.40 (m, 4H), 8.32–8.20 (m, 4H), 7.72–7.52 (m, 12H), 7.50–7.20 (m, 8H), 5.81 (s, 4H), 5.06 (s, 4H), 4.34 (s, 4H), 2.47 (s, 6H), 2.39 (s, 6H). IR (cm$^{-1}$): 1626. MS-ESI: 969.5 (M$^+$+3MeOH−3H$_2$O+H). Anal. calcd for C$_{58}$H$_{56}$B$_2$N$_4$O$_6$·2H$_2$O: C, 72.28; H, 6.07; N, 5.82. Found: C, 72.27; H, 6.05; N, 5.87.

Diboronic acid 7r. Yield 65%. $^1$H NMR (CD$_3$OD) δ 8.60–8.42 (m, 4H), 8.40–8.30 (m, 4H), 7.80–7.52 (m, 10H), 7.50–7.20 (m, 10H), 7.15–7.00 (m, 4H), 5.81 (s, 4H), 5.04 (s, 4H), 4.35 (s, 4H), 2.54 (s, 6H), 2.40 (s, 6H). IR (cm$^{-1}$): 1616. MS-ESI: 1029.5 (M$^+$+2MeOH−3H$_2$O+H).

Diboronic acid 7s. Yield 58%. $^1$H NMR (CD$_3$OD) δ 8.55–8.50 (m, 4H), 8.40–8.25 (m, 4H), 7.72–7.52 (m, 8H), 7.44–7.20 (m, 8H), 5.77 (s, 4H), 5.16 (s, 4H), 4.40 (s, 4H), 2.86–2.78 (m, 2H), 2.64 (s, 6H), 2.47 (s, 6H), 2.20–2.08 (m, 2H), 1.70–1.56 (m, 2H). IR (cm$^{-1}$): 1634. MS-ESI: 961.5 (M$^+$+2MeOH−2H$_2$O+H).

Diboronic acid 7t. Yield 70%. $^1$H NMR (CD$_3$OD) δ 8.50–8.40 (m, 4H), 8.38–8.24 (m, 4H), 7.76–7.52 (m, 10H), 7.40–7.24 (m, 6H), 5.70 (s, 4H), 5.10 (s, 4H), 4.40 (s, 4H), 2.80–2.62 (m, 2H), 2.66 (s, 6H), 2.44 (s, 6H), 1.90–1.74 (m, 2H), 1.70–1.60 (m, 2H). IR (cm$^{-1}$): 1634. MS-ESI: 960.4 (M$^+$+2MeOH−2H$_2$O). Anal. calcd for C$_{58}$H$_{62}$B$_2$N$_4$O$_6$·3H$_2$O: C, 70.59; H, 6.95; N, 5.82. Found C, 70.56; H, 6.35; N, 5.81.

Diboronic acid 7u. Yield 31%. $^1$H NMR (CD$_3$OD+CDCl$_3$) δ 8.68–8.50 (m, 4H), 8.33–8.31 (m, 4H), 7.92–7.90 (m, 4H), 7.65–7.62 (m, 12H), 7.34–7.20 (m, 6H), 5.93 (s, 4H), 5.10 (s, 4H), 4.35 (s, 4H), 2.59 (s, 6H), 2.43 (s, 6H). IR (cm$^{-1}$): 1613. MS-ESI: 959.4 (M$^+$−H$_2$O+H).

Diboronic acid 7v. Yield 49%. $^1$H NMR (CD$_3$OD+CDCl$_3$) δ 8.42–8.40 (m, 4H), 8.29–8.26 (m, 4H), 7.69 (m, 2H), 7.60–7.55 (m, 8H), 7.37–7.25 (m, 8H), 5.82 (s, 4H), 5.02 (s, 4H), 4.31 (s, 4H), 2.76 (s, 6H), 2.39 (s, 6H). IR (cm$^{-1}$): 1614. MS-ESI: 915.4 (M$^+$−H$_2$O+H).

Diboronic acid 7w. Yield 65%. $^1$H NMR (CD$_3$OD+CDCl$_3$) δ 8.53–8.49 (m, 4H), 8.33–8.31 (m, 4H), 7.68–7.60 (m, 10H), 7.37–7.22 (m, 9H), 5.84 (s, 4H), 5.07 (s, 4H), 4.33 (s, 4H), 2.56 (s, 6H), 2.41 (s, 6H). IR (cm$^{-1}$): 1631. MS-ESI: 910.4 (M$^+$−H$_2$O+H).

Diboronic acid 7x. Yield 45%. $^1$H NMR (CD$_3$OD+CDCl$_3$) δ 8.44–8.40 (m, 4H), 8.32–8.22 (m, 4H), 7.78–7.64 (m, 2H), 7.58–7.56 (m, 8H), 7.37–7.28 (m, 6H), 5.69 (s, 4H), 5.08 (s, 4H), 4.31 (s, 4H), 2.60 (s, 6H), 2.44–2.37 (m, 10H), 1.80–1.60 (m, 4H), 1.35–1.27 (m, 20H). IR (cm$^{-1}$): 1637. MS-ESI: 1029.6 (M$^+$−H$_2$O+H).

Diboronic acid 7y. Yield 91%. $^1$H NMR (CD$_3$OD+CDCl$_3$) δ 8.40–7.40 (m, 24H), 5.63 (s, 4H), 4.70 (s, 4H), 4.10 (s, 4H), 2.56 (s, 6H), 2.47 (t, J=7.0 Hz, 4H), 2.30 (s, 6H), 1.99–1.60 (m, 4H). ESI-MS: 889.6 (M$^+$−H$_2$O+H). Anal. calcd. for C$_{56}$H$_{60}$B$_2$N$_4$O$_6$: C, 74.18; H, 6.67; N, 6.18. Found C, 74.55; H, 7.00; N, 5.75.

Diboronic acid 7z. Yield 98%. $^1$H NMR (CD$_3$OD+CDCl$_3$) δ 8.66–8.58 (m, 4H), 8.24–8.08 (m, 4H), 8.00–7.20 (m, 22H), 6.10–5.74 (m, 4H), 4.80 (s, 4H), 4.19 (s, 4H), 2.36 (s, 6H), 2.29 (s, 6H). ESI-MS: 959.5 (M$^+$−H$_2$O+H).

Example 4

General Experimental Methods for sLex Detection

Cell culture. HEPG2 and COS7 cells were maintained in RPMI media (G. E. Moore et al. (1967) *J. Am. Med. Assoc.* 199, 519–524) with 10% FBS (GIBCO). HEP3B cells were maintained in RPMI with 10% FBS and 1× sodium pyruvate and 1× non-essential amino acids (GIBCO).

Flow cytometry analysis. Cell lines HEPG2, HEP3B, and COS7 were prepared and stained with monoclonal anti-carbohydrate antibodies at saturating concentrations as described in R. Nakaya et al. (1994) *J. Gastroenterol.* 29, 24–30; and E. C. M. Brinkman-Van der Linden et al. (1996) *J. Biol. Chem.* 271, 14492–14495. Anti-SSEA-1 (anti-Lewis X) was used at a dilution of 1:1000, anti-Lewis Y (clone F3, Calbiochem, and clone A70-C/C8, NeoMarkers) at a dilution of 1:20, anti-sialyl Lewis X (CSLEX-1 and KM93) at 10 μg/ml, and anti-sialyl Lewis a (CSLEA-1) at 1:500. Cells were then stained with fluorescein isothiocyanate-conjugated goat anti-mouse IgM or anti-mouse IgG. FITC-conjugated murine IgG1/IgG2 and anti-CD18 antibodies (negative controls throughout) were used according to the manufacturer's instructions. Cells were analyzed on a Becton-Dickinson FACScan as previously described in Nakaya et al. and Brinkman-Van der Linden, supra.

Fluorescent labeling studies. 6-well plates were seeded with 1×10$^6$ cells per well and incubated at 37° C. and 5% CO$_2$ for 48 h. The media was removed and cells were washed twice with 1×PBS. The cells were fixed with 1.5 mL of 1:1 methanol/PBS and incubated 20 minutes at 4° C. After incubation, the methanol/PBS solution was removed and cells were washed twice with PBS.

Diboronic acid compounds 7 were resuspended in 1:1 methanol/PBS and added to wells at 0.5 to 10 μM concentrations. One well was incubated only in methanol/PBS without compound as a negative control. The plates were then incubated in darkness at 4° C. for 45 min. Plates were examined with phase contrast microscopy followed by fluorescent microscopy (blue cube wavelengths 370 nm excitation, 426 nm emission; 20× lens). Plates were photographed using a Nikon DXM1200 digital camera and images captured with the Nikon ACT-1 program (v 2.10). The phase contrast and fluorescent images were then overlaid, organized and labeled using Adobe Photoshop 6.0. The images were quantified with NIH ImageJ 1.28. The units (mean gray value) were subtracted from background, where there are no cells. The fluorescent signal was stable for at least 96 h when cells were maintained in darkness.

Example 5

Binding of Fluorescent Compounds 7 to sLex in Solution

Figure 4:
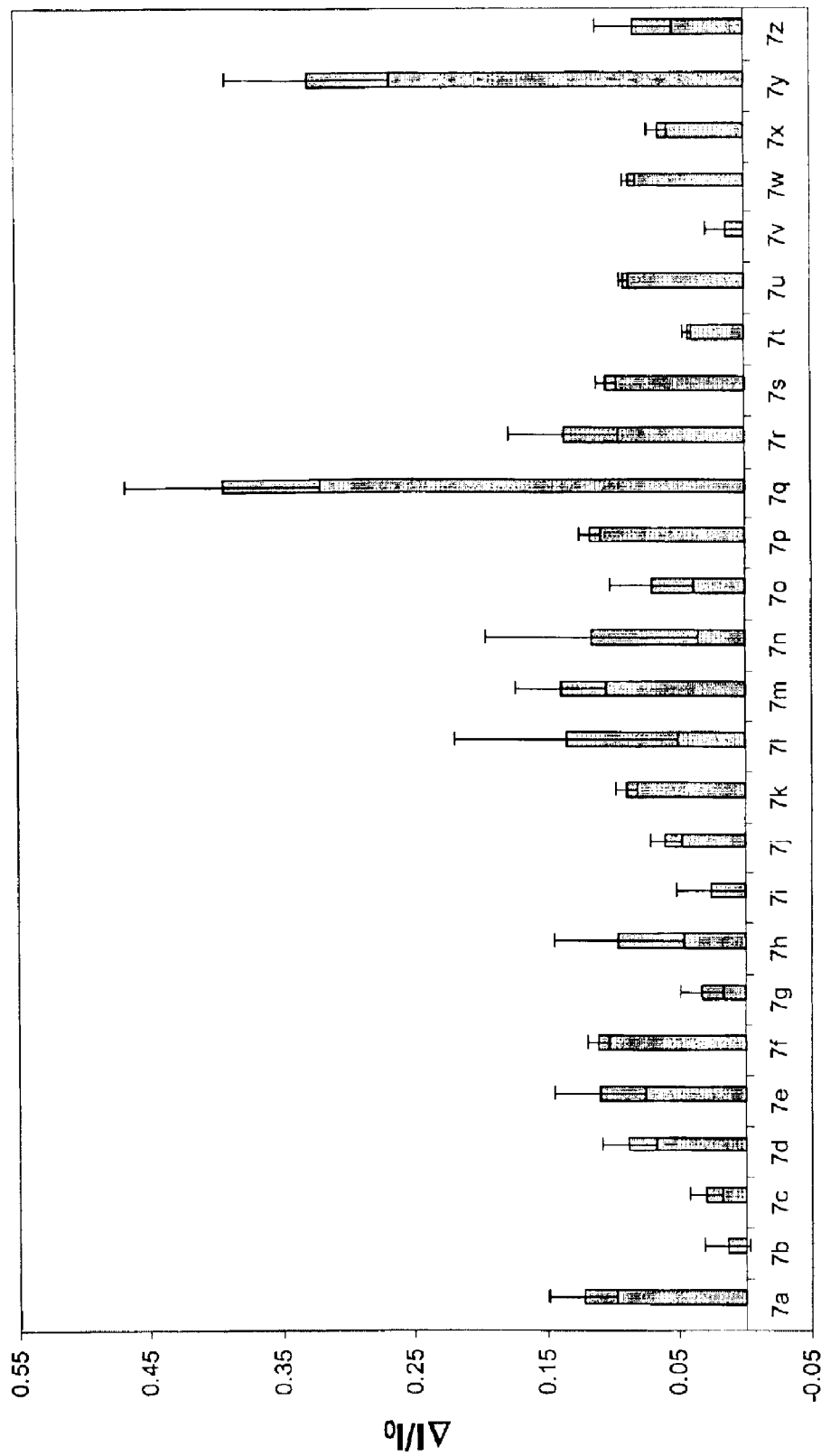
FIG. 4 is a bar graph illustrating the fluorescence intensity change profile of the diboronic acids 7a–z ($1\times10^{-5}$ or $1\times10^{-6}$ M) upon binding with cell surface carbohydrate sLex, where [sLex]=$6\times10^{-5}$ M, $\lambda_{ex}$=370 nm, and $\lambda_{em}$=426 nm. Data represented in FIG. 4 was generated under the experimental conditions described in Examples 4 and 5, below.

Diboronic acid compounds 7 were designed to show significant fluorescence intensity changes upon binding with a complementary carbohydrate. In screening for their binding with the target carbohydrate, sLex, the fluorescence intensity changes of solutions of the compounds upon addition of the carbohydrate were determined. These experiments were conducted in a mixture of methanol and 0.1 M phosphate buffer (pH 7.4) (1:1, v/v). Methanol was used to improve the solubility of the sensor compounds. The concentration of fluorescent sensor compound (7) (specific structures provided in FIG. 1, above) was fixed at 1×10$^{-5}$ or 1×10$^{-6}$ M, and the concentration of sLex was set at 60 μM. The fluorescence intensity change profile for these diboronic acids is shown in FIG. 4. As illustrated in the Figure, these compounds showed varying degrees of fluorescence intensity changes upon addition of sLex, indicating varying degrees of affinity for the carbohydrate. Among them, compound 7q showed the greatest fluorescence intensity change upon mixing with sLex.

Example 6

Selective Binding of Compound 7q to sLex on Cell Surfaces

After demonstration of binding of the fluorescent sensor compounds 7 to sLex in solution, the compound 7q was tested to see if it could bind the biomarker sLex on cell surfaces. HEPG2, a cell line that selectively expresses sLex on the surface, was selected for examination. To examine the selectivity of the sensor for cell surface sLex, HEP3B and COS7 cells were labeled in parallel. COS7 expresses none of the fucosylated antigens associated with carcinoma progression and HEP3B expresses only the Lewis Y antigen. See B. W. Weston et al. (1992) *J. Biol. Chem.* 267, 4152–4160; B. W. Weston et al. (1992) *J. Biol. Chem.* 267, 24575–24584.

Figure 5:
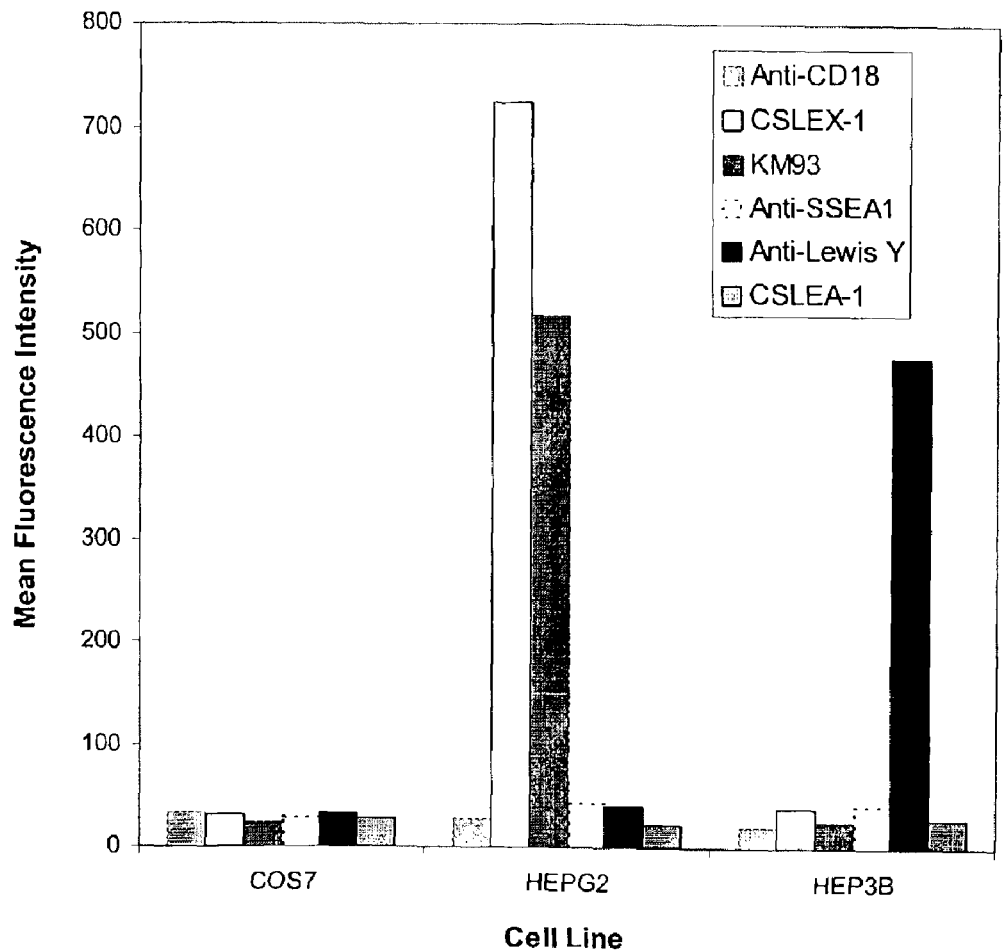
FIG. 5 is a bar graph illustrating the flow cytometry analysis of surface antigens on HEPG2, HEP3B, and COS7 cells, as detailed in Example 6, below. Briefly, cells were harvested, stained with monoclonal antibodies, and subjected to flow cytometric analysis as described in the Examples. Anti-CD18 results are presented as negative controls. Monoclonal antibodies CSLEX-1 and KM93 both recognize sLex. Data presented in FIG. 5 are the representative mean fluorescence intensity values from four experiments. The antigen-positive population of HEPG2 and HEP3B cells was gated at $1.5\times10^{1}$ units, and over 95% of stained cells were identified by these procedures with each primary antibody used.

Flow cytometry analysis of HCC lines with anti-carbohydrate monoclonal antibodies was performed to characterize surface glycan expression. Using two different monoclonal antibodies directed at sLex, HEPG2 cells were found to express high levels, while HEP3B cells expressed little or none (FIG. 5). Anti-Lewis Y monoclonal antibodies revealed the converse: high expression on HEP3B and little or no staining of HEPG2. None of the cell lines expressed Lewis X or sialyl Lewis a, related antigens expressed on other forms of carcinoma. These cell lines were then used for the fluorescent labeling studies with the sensors.

Figure 6:
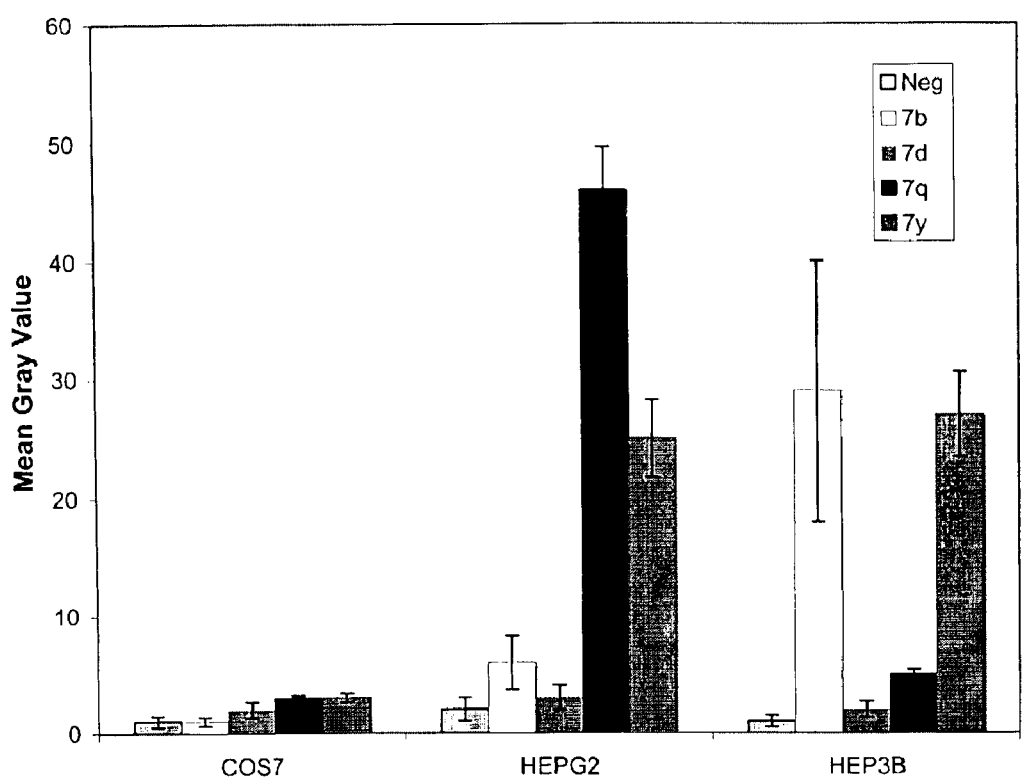
FIG. 6 is a bar graph illustrating the densitometry quantification of fluorescent compounds binding to HCC and control cell lines, as detailed in Example 6. Briefly, cells were labeled with 1 $\mu$M of fluorescent sensor compounds 7b, 7d, 7y, and 7q. One well was incubated in methanol/PBS only (without compound) as a negative control ("neg"). Mean gray values (y-axis) were determined after subtraction of cell-free background. Results from five experiments are summarized.

HEPG2 and control cell lines were incubated with compound 7q, while three other diboronic acids (7b, 7d, 7y) were used as controls. The cells lines were examined under fluorescent microscopy and photographed. Images were subjected to densitometry measurement as described in experimental procedures. As seen with sLex solution binding studies summarized in FIG. 4, Compound 7q was highest in mean gray value when binding HEPG2 cells expressing sLex (FIG. 6). Compound 7q did not recognize Lewis Y on HEP3B cells. Compound 7b avidly bound Lewis Y-expressing HEP3B cells, which correlates with solution binding studies using 7b and Lewis Y (data not shown). Compound 7b did not recognize sLex on HEPG2 cells at this concentration (1 $\mu$M), again correlating with solution binding studies (FIG. 4). Even at this relatively low concentration, compound 7y recognized surface sLex and Lewis Y with equal avidity, concordant with solution binding studies (data not shown). Compound 7d, which had low affinity for both sLex and Lewis Y in solution, did not label HEPG2 or HEP3B. None of the compounds bound to COS7 cells at any of the concentrations tested. The above results showed that the cell labeling corresponded with the solution binding studies using fluorimetry.

Figure 7:
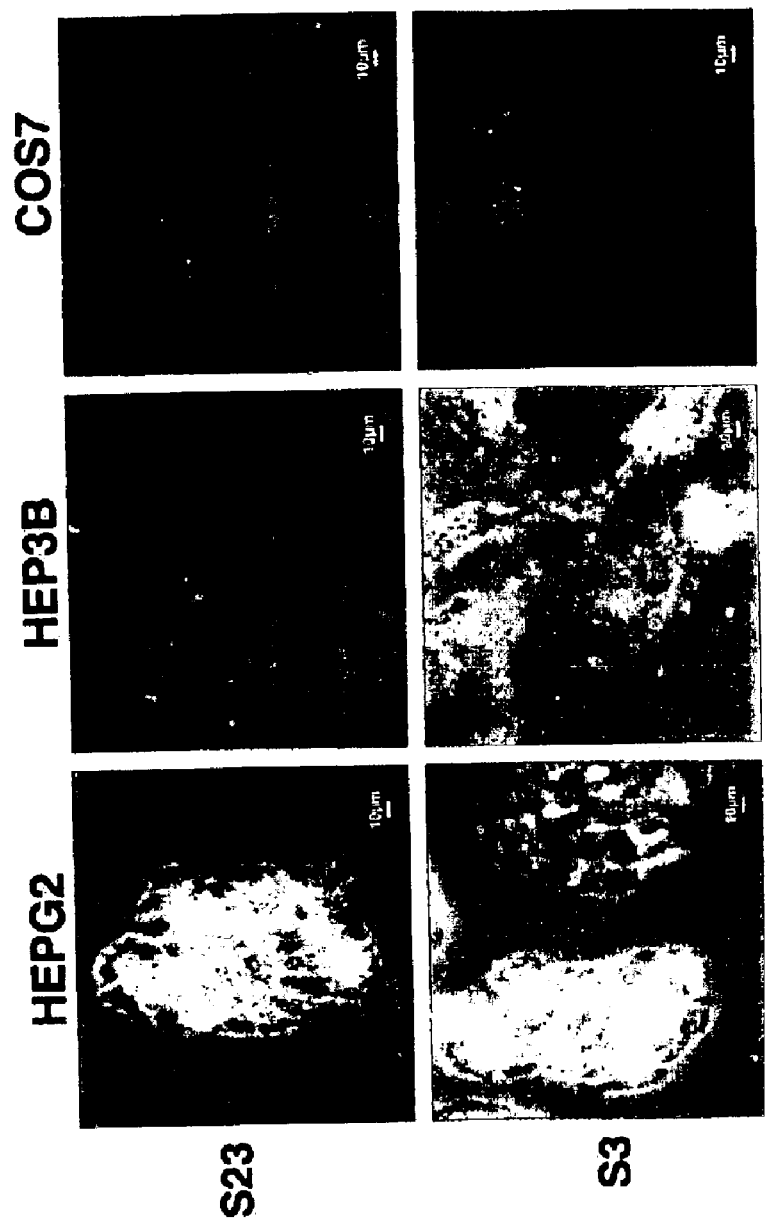
FIG. 7 displays photographs of representative fluorescent labeling studies of HEPG2, HEP3B, and COS7 cells, as detailed in Example 6. HEPG2 cells express only sLex, HEP3B cells express only Lewis Y, and COS7 cells do not express either antigen. Compounds 7q (S-23) and 7b (S-3) are used at 5 $\mu$M in the examples shown. Excitation wavelength=370 nm and emission wavelength=426 nm. Scale in lower right corner indicates 10 micrometer length.

Images from a representative cell-labeling experiment are shown in FIG. 7. HCC and control cell lines were incubated with compound 7q, examined under phase contrast and fluorescent microscopy, and digitally photographed as described in experimental procedures. As expected, compound 7q labeled only HEPG2 cells, exhibiting dose-responsive fluorescence over the range of 0.5–10 $\mu$M. Even at higher concentrations, (e.g. 5 $\mu$M, FIG. 7), 7q did not recognize Lewis Y on HEP3B cells. Thus, sensor 7q appears to have both high sensitivity and specificity for sLex when compared to related compounds and carbohydrate antigens.

Example 7

Selective Binding of Fluorescent Sensor Compounds to Glucose

Figure 8:
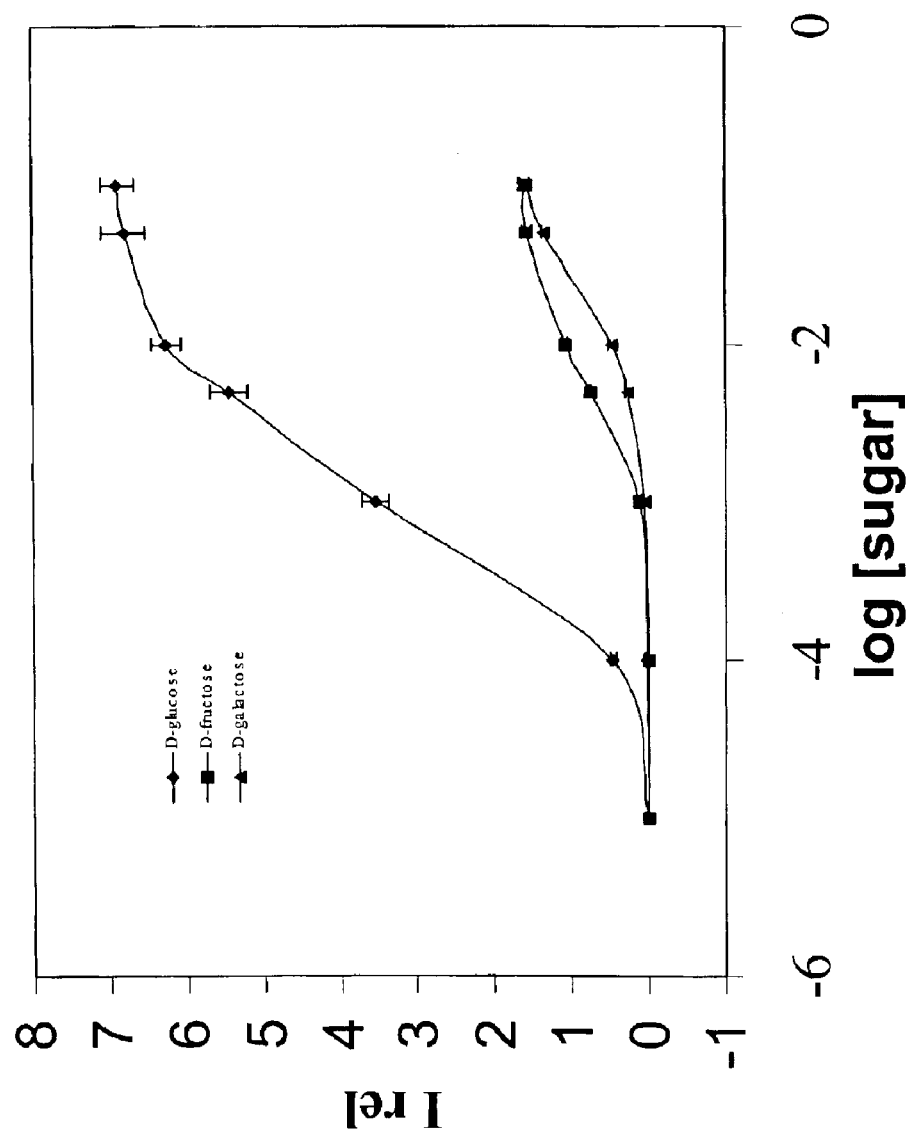
FIG. 8 is a graph illustrating the relative fluorescence intensity $I_{rel}$ of fluorescent compound 7b as function of the saccharide concentrations at 25° C.; $1.0\times10^{-6}$M in 50% MeOH/0.1 M aqueous phosphate buffer at pH 7.4; $\lambda_{ex}$=370 nm; $\lambda_{em}$=423 nm. Data represented in FIG. 8 was generated using the experimental conditions and methods described in Example 7, below. Data points represented as diamonds are data points for D-glucose; data points represented as squares are data points for D-fructose, and data points represented as triangles are data points for D-galactose.

The affinity and selectivity of the fluorescent sensor compounds (7) for glucose were evaluated. Specifically, 2 mL of a solution of each sensor compound (7) in methanol ($2 \times 10^{-6}$ M) was mixed with 2 mL of aqueous saccharide phosphate buffer solution (pH 7.4) at various concentrations, and the fluorescence intensity recorded. Among the compounds prepared (see Table 1), fluorescent sensor compound 7b showed the highest selectivity for glucose over fructose and galactose with a $K_a$ of 1472, 34, and 30 $M^{-1}$, respectively. This represents a 43- and 49-fold selectivity over fructose and galactose, respectively. The results of this evaluation are shown in FIG. 8. In addition, fluorescence enhancement was very large (about 7-fold).

It should be noted that the "natural tendency" for boronic acid is to favor the binding with fructose over glucose. See, Springsteen et al., supra, and Lorand et al., supra. For example, phenylboronic acid (PBA) has a $K_a$ of 162 $M^{-1}$ for fructose and 5 $M^{-1}$ for glucose. Springsteen et al., supra. Sensor compound 7b represents an improvement of about 300-fold in affinity and about 1400-fold improvement in selectivity for glucose over fructose compared with simple PBA. It should also be noted that sensor 7b showed the most sensitive fluorescence intensity changes to glucose in the mM region (FIG. 8), which is the most physiologically relevant concentration range in terms of blood glucose detection.

Example 8

Complex Formation between Compound 7b and Glucose

The observed selectivity of compound 7b for glucose implies the formation of a bidentate complex between glucose and 7b. See Norrild (1995), supra; Eggert, supra; M. Bielecki et al., *J. Chem. Soc., Perkin Trans.* 2 (1999), 449–455; and J. C. Norrild and H. Eggert (1996) *J. Chem. Soc. Perkin Trans.* 2, 2583–2588. $^1$H-NMR techniques were used to confirm the formation of the complex between 7b and glucose. Specifically, 7b and D-glucose in a 1:1 ratio were dissolved in methanol-$d_4$ containing 1% of $D_2O$. Norrild and co-workers have conducted a detailed examination of D-glucose binding with a diboronic acid compound using 1H-NMR, and found that in the initial complex, glucose was in the $\alpha$-D-glucopyranose form. Id. However, with time this complex is converted to the thermodynamically more stable $\alpha$-D-glucofuranose form. It is known that water facilitates this mutarotation of the $\alpha$-D-glucopyranose to $\alpha$-D-glucofuranose. Therefore, in the present study, a small amount of $D_2O$ (1%) was used to aid the mutarotation to the more thermodynamically stable form.

The $^1$H-NMR spectrum obtained 20 minutes after mixing 7b and glucose showed the appearance of new peaks compared with the two starting materials, the most obvious peaks of which were in the region from 2.5 to 2.8 ppm. After the mixture was kept at $-20°$ C. for two weeks, the two peaks at 2.08 and 2.25 ppm corresponding to the N—$CH_3$'s of the free 7b almost completely disappeared, and four new peaks in the range from 2.5 to 2.8 ppm corresponding to the N—$CH_3$'s of the complex appeared. Such results indicate the formation of a 1:1 complex since the two starting materials were added in a 1:1 ratio. $^1$H-$^1$H-COSY, $^1$H—$^{13}$C Heterocorrelated spectra (HMQC and HMBC), TOCSY, and selective decoupling experiments were performed to give a reasonable assignment. In the proton spectrum, coupling constant between H2 and H3 is about zero ($J_{2,3} \sim 0$) and no cross peaks were found between these two protons in $^1$H-$^1$H-COSY, TOCSY, and ROESY, indicating that the complex was in the form of $\alpha$-D-glucofuranose.

The electrospray ionization (ESI) mass spectrum showed large peaks at m/z 1063.5 (M+1) for the corresponding 1:1 complex ($C_{66}H_{64}B_2N_4O_8$, M=1062). No peak was observed at m/z 1243 (M+1), which correspond to the 1:2 complex ($C_{72}H_{76}B_2N_4O_{14}$, M=1242). Therefore, MS data also confirmed the predicted formation of a 1:1 complex.

In conclusion, it was determined that the diboronic acid fluorescent sensor compound 7b is selective for glucose. The sensor compound has a high affinity ($K_a$ 1472 $M^{-1}$) and shows a 43- and 49-fold selectivity for glucose over fructose and galactose, respectively. The binding affinity improvement is about 300-fold and the selectivity improvement for glucose over fructose is about 1400-fold compared with the monoboronic acid compound, PBA. The fluorescence intensity change was also very high, up to 7-fold. This is significantly higher than what has been previously observed with other reported glucose sensors. $^1$H-NMR studies indicate that sensor 7b binds with α-D-glucofuranose in a bidentate manner.

It will be understood that various details of the invention may be changed without departing from the scope of the invention. Furthermore, the foregoing description is for the purpose of illustration only, and not for the purpose of limitation, as the invention is defined by the claims as set forth hereinafter.

What is claimed is:

1. A fluorescent sensor compound having the formula:

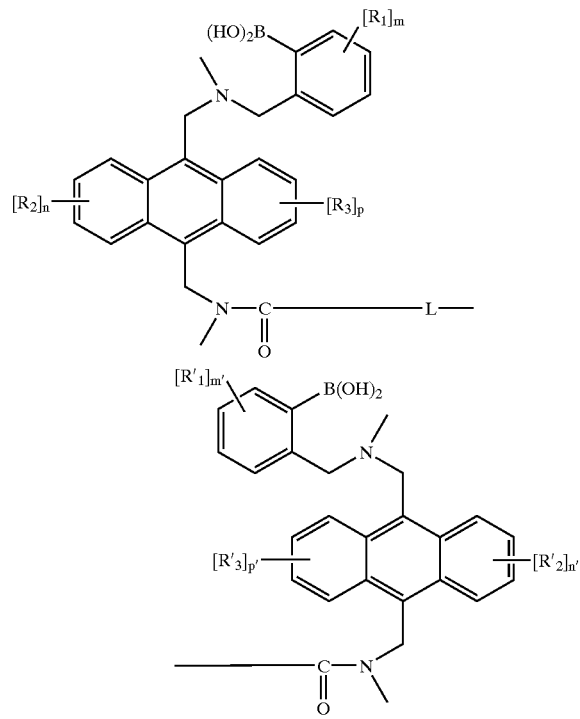

wherein L is selected from the group consisting of alkyl, alkylene, aryl, cycloalkyl, alkoxy, aryloxy, arylalkyl, and arylalkyloxyl;

each m, m', n, n', p, and p' is independently an integer from 0 to 4, inclusive; and each $R_1$, $R'_1$, $R_2$, $R'_2$, $R_3$ and $R'_3$ is independently selected from the group consisting of hydrogen, alkyl, alkylene, aryl, cycloalkyl, alkoxy, aryloxy, arylalkyl, arylalkyloxyl, halo, substituted and unsubstituted amino, and substituted and unsubstituted thiol.

2. The compound according to claim 1, wherein L is selected from the group consisting of $C_2$ to $C_{20}$ alkyl.

3. The compound according to claim 1, wherein L is aryl.

4. The compound according to claim 1, wherein L is selected from the group consisting of:

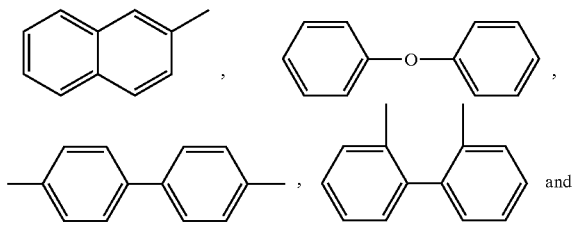

and

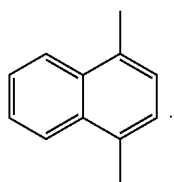

5. The compound according to claim 1, wherein L is selected from the group consisting of:

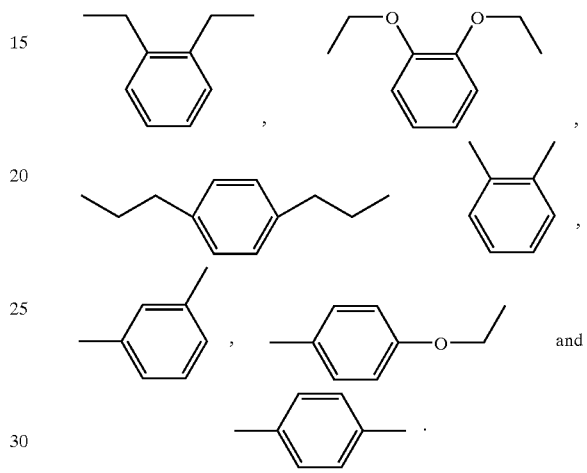

and

6. The compound according to claim 1, wherein m, m', n, n', p, and p' are each zero and L is:

7. The compound according to claim 1, wherein m, m', n, n', p, and p' are each zero and L is:

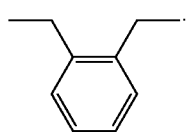

8. The compound according to claim 1, wherein the compound selectively binds a saccharide.

9. The compound according to claim 8, wherein the saccharide is a monosaccharide.

10. The compound according to claim 9, wherein the monosaccharide is glucose.

11. The compound according to claim 8, wherein the saccharide is a polysaccharide.

12. The compound according to claim 11, wherein the polysaccharide is a cell-surface polysaccharide.

13. The compound according to claim 11, wherein the polysaccharide is sialyl Lewis X (sLex).

14. A method of detecting glucose in a biological sample, comprising contacting a biological sample with a fluorescent sensor compound having the formula:

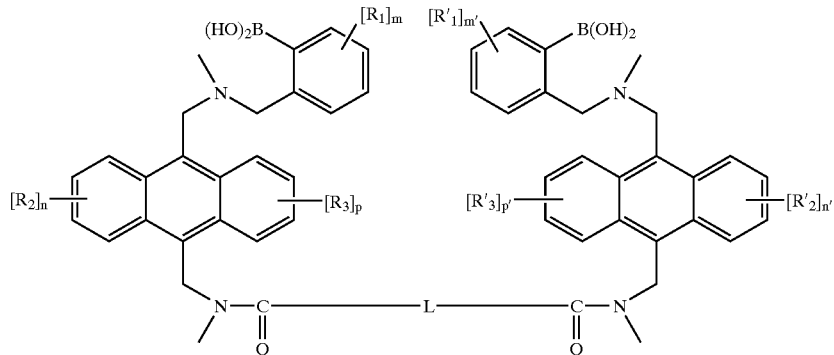

wherein L is selected from the group consisting of alkyl, alkylene, aryl, cycloalkyl, alkoxy, aryloxy, arylalkyl, and arylalkyloxyl;

each m, m', n, n', p, and p' is independently an integer from 0 to 4, inclusive;

each $R_1$, $R'_1$, $R_2$, $R'_2$, $R_3$ and $R'_3$ is independently selected from the group consisting of hydrogen, alkyl, alkylene, aryl, cycloalkyl, alkoxy, aryloxy, arylalkyl, arylalkyloxyl, halo, substituted and unsubstituted amino, and substituted and unsubstituted thiol; and detecting the presence or absence of fluorescence in the sample, wherein the presence of fluorescence indicates the presence of glucose in the sample.

15. The method according to claim 14, further comprising
measuring the amount of fluorescence in the sample; and
correlating the amount of fluorescence in the sample with a concentration of glucose in the sample.

16. The method according to claim 14, wherein m, m', n, n', p, and p' are each zero and L is:

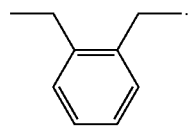

17. The method according to claim 14, wherein the fluorescent sensor compound is provided in an implantable sensor device.

18. A method of detecting sialyl Lewis X in a biological sample, comprising contacting a biological sample with a fluorescent sensor compound having a formula:

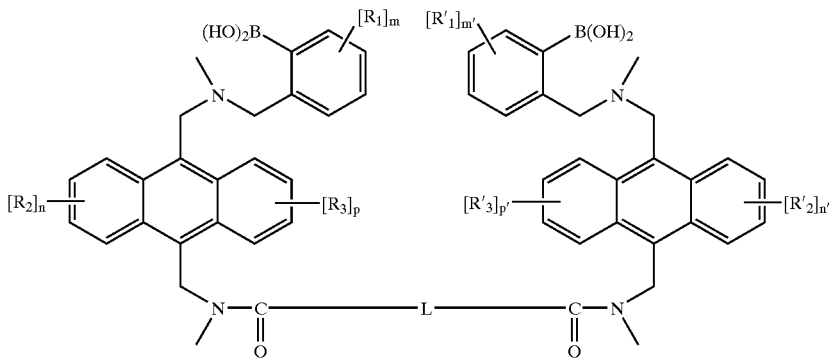

wherein L is selected from the group consisting of alkyl, alkylene, aryl, cycloalkyl, alkoxy, aryloxy, arylalkyl, and arylalkyloxyl;

each m, m', n, n', p, and p' is independently an integer from 0 to 4, inclusive; and each $R_1$, $R'_1$, $R_2$, $R'_2$, $R_3$ and $R'_3$ is independently selected from the group consisting of hydrogen, alkyl, alkylene, aryl, cycloalkyl, alkoxy, aryloxy, arylalkyl, arylalkyloxyl, halo, substituted and unsubstituted amino, and substituted and unsubstituted thiol; and detecting the presence or absence of fluorescence in the sample, wherein the presence of fluorescence indicates the presence of sialyl Lewis X in the sample.

19. The method according to claim 18, further comprising:
measuring the amount of fluorescence in the sample; and
correlating the amount of fluorescence in the sample with a concentration of sialyl Lewis X in the sample.

20. The method according to claim 18, wherein m, m', n, n', p, and p' are each zero and L is:

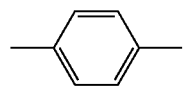

21. A method of detecting cancer cells that express sialyl Lewis X in a biological sample, comprising contacting a biological sample with a fluorescent sensor compound of the formula:

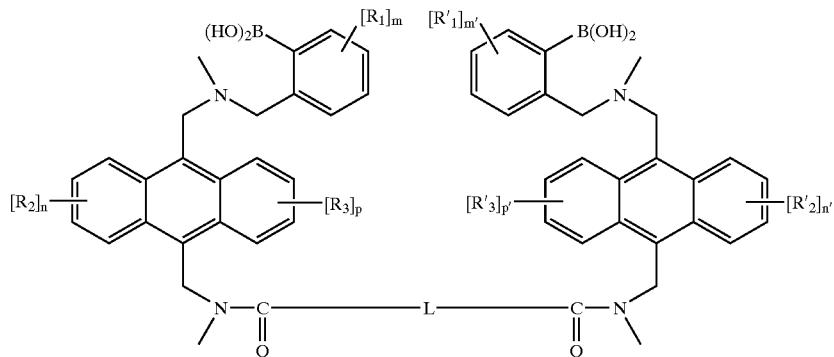

wherein L is selected from the group consisting of alkyl, alkylene, aryl, cycloalkyl, alkoxy, aryloxy, arylalkyl, and arylalkyloxyl;

each m, m', n, n', p, and p' is independently an integer from 0 to 4, inclusive; and each $R_1$, $R'_1$, $R_2$, $R'_2$, $R_3$ and $R'_3$ is independently selected from the group consisting of hydrogen, alkyl, alkylene, aryl, cycloalkyl, alkoxy, aryloxy, arylalkyl, arylalkyloxyl, halo, substituted and unsubstituted amino, and substituted and unsubstituted thiol; and detecting the presence or absence of fluorescence in the sample, wherein the presence of fluorescence indicates the presence of cancerous in the sample.

22. The method according to claim 21, further comprising:

measuring the amount of fluorescence in the sample; and correlating the amount of fluorescence in the sample with the amount of cancerous cells in the sample.

23. The method according to claim 21, wherein m, m', n, n', p, and p' are each zero and L is:

24. The method according to claim 21, wherein the cancer cells are carcinoma cells.

25. The method according to claim 21, wherein the cancer cells are hepatocellular carcinoma cells.

* * * * *